US012174189B2

(12) United States Patent
Berenson et al.

(10) Patent No.: US 12,174,189 B2
(45) Date of Patent: Dec. 24, 2024

(54) DIAGNOSTIC, PROGNOSTIC, AND MONITORING METHODS FOR CHRONIC LYMPHOCYTIC LEUKEMIA

(71) Applicant: INSTITUTE FOR MYELOMA & BONE CANCER RESEARCH, West Hollywood, CA (US)

(72) Inventors: James R. Berenson, West Hollywood, CA (US); Haiming Chen, West Hollywood, CA (US); Eric Sanchez, West Hollywood, CA (US)

(73) Assignee: ONCOTRACKER, INC., West Hollywood, CA (US)

(*) Notice: Subject to any disclaimer, the term of this patent is extended or adjusted under 35 U.S.C. 154(b) by 0 days.

(21) Appl. No.: 16/146,300

(22) Filed: Sep. 28, 2018

(65) Prior Publication Data

US 2019/0107541 A1    Apr. 11, 2019

Related U.S. Application Data

(62) Division of application No. 14/766,694, filed as application No. PCT/US2014/015338 on Feb. 7, 2014, now Pat. No. 10,126,301.

(60) Provisional application No. 61/762,753, filed on Feb. 8, 2013.

(51) Int. Cl.
   *G01N 33/574* (2006.01)
(52) U.S. Cl.
   CPC . *G01N 33/57426* (2013.01); *G01N 33/57407* (2013.01); *G01N 33/57488* (2013.01); *G01N 2333/70578* (2013.01); *G01N 2333/7151* (2013.01); *G01N 2800/52* (2013.01)

(58) Field of Classification Search
   None
   See application file for complete search history.

(56) References Cited

U.S. PATENT DOCUMENTS

| | | |
|---|---|---|
| 4,493,795 A | 1/1985 | Nestor, Jr. et al. |
| 4,816,567 A | 3/1989 | Cabilly et al. |
| 5,712,291 A | 1/1998 | D'amato |
| 6,258,540 B1 | 7/2001 | Lo et al. |
| 6,355,623 B2 | 3/2002 | Seidman et al. |
| 7,598,257 B2 | 10/2009 | Rodgers et al. |
| 10,126,301 B2 | 11/2018 | Berenson et al. |
| 2006/0084055 A1 | 4/2006 | Gaiger et al. |
| 2006/0136136 A1 | 6/2006 | Karpusas |
| 2007/0207474 A1 | 9/2007 | Ansell et al. |
| 2007/0212733 A1 | 9/2007 | Martin |
| 2008/0050381 A1 | 2/2008 | Takeuchi et al. |
| 2008/0058316 A1 | 3/2008 | Eberhart et al. |
| 2008/0268480 A1 | 10/2008 | Hsu et al. |
| 2008/0312259 A1 | 12/2008 | Rodgers et al. |
| 2009/0191203 A1 | 7/2009 | Belloir et al. |
| 2010/0285020 A1 | 11/2010 | Aifantis et al. |
| 2013/0101599 A1 | 4/2013 | Borges et al. |
| 2014/0193433 A1 | 7/2014 | Borges et al. |
| 2014/0220014 A1 | 7/2014 | Dillon et al. |
| 2016/0131654 A1 | 5/2016 | Berenson et al. |
| 2016/0331754 A1 | 11/2016 | Dansey et al. |
| 2017/0106003 A1 | 4/2017 | Berenson |
| 2017/0224730 A1 | 8/2017 | Berenson |
| 2017/0239351 A1 | 8/2017 | Hamdy et al. |
| 2018/0080085 A1 | 3/2018 | Pockaj et al. |
| 2018/0306791 A1 | 10/2018 | Bounds et al. |
| 2019/0049437 A1 | 2/2019 | Berenson |
| 2020/0326339 A1 | 10/2020 | Berenson |
| 2022/0000872 A1 | 1/2022 | Berenson et al. |

FOREIGN PATENT DOCUMENTS

| | | | |
|---|---|---|---|
| EP | 0937461 B1 | 7/2005 | |
| EP | 2762496 A1 | 8/2014 | |
| JP | 2019501369 A | 1/2019 | |
| WO | WO 2002/068414 A2 | 9/2002 | |
| WO | WO 2004/081043 A2 | 9/2004 | |
| WO | WO 2006/044582 A2 | 4/2006 | |
| WO | WO 2007/131092 A2 | 11/2007 | |
| WO | WO 2010/104949 A2 | 9/2010 | |
| WO | WO-2012163805 A1 * | 12/2012 | ............. A61K 38/05 |
| WO | WO 2014/068079 A1 | 5/2014 | |
| WO | WO 2014/124280 A1 | 8/2014 | |
| WO | WO 2015/166073 A1 | 11/2015 | |
| WO | WO-2016061142 A1 | 4/2016 | |
| WO | WO 2016/090320 A1 | 6/2016 | |
| WO | WO 2017/019496 A1 | 2/2017 | |
| WO | WO 2017/031104 A1 | 2/2017 | |
| WO | WO 2017/072716 A1 | 5/2017 | |
| WO | WO 2017/123741 A1 | 7/2017 | |

(Continued)

OTHER PUBLICATIONS

Concise Medical Dictionary (serum 2010) (Year: 2010).*
Avrameas, et al., "Coupling of Enzymes to Antibodies and Antigens." Scand. J Immunol. (1978); vol. 8 Suppl. 7: 7-23.
Bellucci, et al., "Graft-versus-tumor response in patients with multiple myeloma is associated with antibody response to BCMA, a plasma-cell membrane receptor." Blood (2005); 105(10): 3945-3950.
Benboubker, et al., "A new serologic index for low-grade non-Hodgkin's lymphoma based on initial CA125 and LDH serum levels." Annals of Oncology (2000); 11:1485-1491.
Bladé, J., et al., "Criteria for evaluating disease response and progression in patients with multiple myeloma treated by high-dose therapy and haemopoietic stem cell transplantation. Myeloma Subcommittee of the EBMT. European Group for Blood and Marrow Transplant." Br J Haematol. (1998); 102(5): 1115-1123.

(Continued)

Primary Examiner — Peter J Reddig
(74) Attorney, Agent, or Firm — Stites & Harbison, PLLC; Mandy Wilson Decker; Patrick M. Torre

(57) ABSTRACT

The invention generally provides improved compositions and methods for detecting, diagnosing, prognosing, and monitoring multiple myeloma, chronic lymphocytic leukemia, or B-cell non-Hodgkin lymphoma in a subject. In particular, the invention provides methods for detecting BCMA in subjects to reliably diagnose, predict survival, or monitor multiple myeloma, chronic lymphocytic leukemia, or B-cell non-Hodgkin lymphoma in the subject.

17 Claims, 17 Drawing Sheets

(56) References Cited

FOREIGN PATENT DOCUMENTS

| WO | WO 2017/201040 A1 | 11/2017 |
|----|---|---|
| WO | WO-2018026819 A2 | 2/2018 |
| WO | WO 2018/085363 A2 | 5/2018 |
| WO | WO 2018/231944 A1 | 12/2018 |
| WO | WO-2019018603 A2 | 1/2019 |
| WO | WO 2020/092792 A2 | 5/2020 |

OTHER PUBLICATIONS

Boerner, et al., "Production of antigen-specific human monoclonal antibodies from in vitro-primed human splenocytes," J. Immunol. (1991); 147 (1): 86-95.

Borges, et al., "Chorioallantoic Membrane Angiogenesis Model for Tissue Engineering: A New Twist on a Classic Model." Tissue Engineering (2003); 9 (3): 441-450.

Campbell and Berenson, "Animal Models of Multiple Myeloma and Their Utility in Drug Discovery," Current Protocols in Pharmacology Chapter 14, Unit 14.9.1, Supplement 40 (Mar. 2008).

Cheema, et al., "Elevated Serum B Lymphocyte Stimulator Levels in Patients With Systemic Immune-Based Rheumatic Diseases" Arthritis & Rheumatism, 44(6):1313-1319 (2001).

Chiu, et al., "Hodgkin lymphoma cells express TACI and BCMA receptors and generate survival and proliferation signals in response to BAFF and APRIL," Blood (2007); 109 (2): 729-739.

Chiu, et al., "The TNF family members BAFF and APRIL play an important role in Hodgkin lymphoma." Blood (2005); 106 (11, part 1 ): pp11A), BIOSIS Accession No. 2006: 180280, 47th Annual Meeting of the American Society of Hematology, Dec. 10-13, 2005, Meeting Abstract, 2 pages.

Chou and Talalay, "Quantitative analysis of dose-effect relationships: the combined effects of multiple drugs or enzyme inhibitors." Adv Enzyme Regul. (1984); 22: 27-55.

Christiansen, et al., "Serum Levels of Soluble Intercellular Adhesion Molecule 1 Are Increased in Chronic B-Lymphocytic Leukemia and Correlate With Clinical Stage and Prognostic Markers," Blood (1994); 84 (9): 3010-3016.

Chuaqui, et al., "Post-analysis follow-up and validation of microarray experiments," Nature Genetics (2002); Supplement 32: 509-514.

Churchill, "Fundamentals of experimental design for CDNA microarrays," Nature Genetics (2002); Supplement 32: 490-495.

Clackson, et al., "Making antibody fragments using phage display libraries," Nature (1991); 352: 624-628.

Day, et al., "Selectivity of BAFF/BLyS and APRIL for binding to the TNF family receptors BAFFR/BR3 and BCMA," Biochemistry (2005); 44: 1919-1931.

Durie, B.G.M., et al. "International uniform response criteria for multiple myeloma." Leukemia (2006); 20 (9): 1467-1473.

Elsawa, et al., "B-lymphocyte stimulator (BLyS) stimulates immunoglobulin production and malignant B-cell growth in Waldenstrom macroglobulinemia." Blood (2006); 107 (7): 2882-2888.

EP Application No. 14748765.6, Supplementary European Search Report dated Aug. 2, 2016, 7 pages.

EP Application No. 15800211.3, Partial Supplementary European Search Report dated Dec. 14, 2017, 10 pages.

EP Application No. 15800211.3, Supplementary European Search Report dated Dec. 12, 2017, 21 pages.

EP Application No. 15807258.7, Extended European Search Report dated Jan. 4, 2018, 11 pages.

Gordon, et al., "Identification of Novel Receptors on Myeloma Cells and Monocytes That Contribute to Myeloma Tumor Proliferation and Angiogenesis." Blood (2005); 106 (11): 2507.

Gras, et al., "BCMAp: an integral membrane protein in the Golgi apparatus of human mature B lymphocytes," International Immunology (1995); 7 (7): 1093-1106.

Greipp, et al., "International Staging System for Multiple Myeloma." Journal of Clinical Oncology (2005); 23(15): 3412-3420.

Groom, et al., "Association of BAFF/BLyS overexpression and altered B cell differentiation with Sjögren's syndrome," Journal of Clinical Investigation (2002); 109 (1): 59-68.

Gross, et al., "TACI and BCMA are receptors for a TNF homologue implicated in B-cell autoimmune disease," Nature (2000); 404: 995-999.

Hamblin and Hamblin, "The Immunodeficiency of Chronic Lymphocytic Leukaemia," British Medical Bulletin (2008); 87 (1): 49-62.

Holloway et al., "Options available-from start to finish-for obtaining data from DNA Microarrays II," Nature Genetics (2002); Supplement 32: 481-489.

Hoogenboom, et al., "By-passing Immunisation Human Antibodies from Synthetic Repertoires of Germline VH Gene Segments Rearranged in Vitro," J. Mol. Biol. (1992); 227: 381-388.

Hornbeck, et al., "Enzyme-Linked Immunosorbent Assays (ELISA)." Current Protocols in Molecular Biology (1991), 11.2.1-11.2.22, 22 pages.

Huerta-Yepez, et al., "Overexpression and Preferential Nuclear Translocation of the Transcription Factor Yin Yang 1 (YY1) in Human Bone Marrow-Derived Multiple Myeloma." Blood (2005); 106 (11): 3394.

International Preliminary Report on Patentability for International Application No. PCT/US2015/035023, dated Dec. 15, 2016, 5 pages.

International Search Report and Written Opinion for International Application No. PCT/US2015/035023, mailed Sep. 22, 2015, 7 pages.

International Preliminary Report on Patentability for International Application No. PCT/US2009/063316, dated May 10, 2011, 5 pages.

International Preliminary Report on Patentability for International Application No. PCT/US2014/015338, dated Aug. 11, 2015, 8 pages.

International Preliminary Report on Patentability for International Application No. PCT/US2015/032869, dated Nov. 29, 2016, 8 pages.

International Preliminary Report on Patentability for International Application No. PCT/US2016/043536, dated Jan. 30, 2018, 5 pages.

International Preliminary Report on Patentability for International Application No. PCT/US2017/013169, dated Jul. 17, 2018, 6 pages.

International Search Report and Written Opinion for International Application No. PCT/US2009/063316, mailed Feb. 3, 2010, 8 pages.

International Search Report and Written Opinion for International Application No. PCT/US2014/015338, mailed Jul. 16, 2014, 11 pages.

International Search Report and Written Opinion for International Application No. PCT/US2016/043536, mailed Oct. 7, 2016, 7 pages.

International Search Report and Written Opinion for International Application No. PCT/US2017/013169, mailed Apr. 10, 2017, 8 pages.

International Search Report and Written Opinion for International Application No. PCT/US2017/032894, mailed Aug. 29, 2017, 8 pages.

International Search Report and Written Opinion, for International Application No. PCT/US2015/032869, mailed Aug. 7, 2015, 10 pages.

Iris, et al., "Prevention of Minimal Residual Disease in Ph plus AL", Database accession No. PREV201400360357, Database Biosis [Online], Biosciences Information Service, Philadelphia, PA, US, Nov. 2013; & Blood, vol. 122, No. 21, Nov. 2013 (Nov. 2013), p. 1265, 55th Annual Meeting of the American Society of Hematology; New Orleans, LA, USA, Dec. 7-10, 2013, ISSN: 0006-4971 (print).

Jäger, et al., "Serum levels of the angiogenic factor pleiotrophin in relation to disease stage in lung cancer patients." British Journal of Cancer (2002); 86 (6): 858-863.

Jones, et al., "Replacing the complementarity-determining regions in a human antibody with those from a mouse," Nature (1986); 321: 522-525.

Jones, et al., "The soluble interleukin 6 receptor: mechanisms of production and implications in disease," Faseb J. (2001); 15: 43-58.

(56) References Cited

OTHER PUBLICATIONS

Källander, et al., "Serum deoxythymidine kinase gives prognostic information in chronic lymphocytic leukemia." Cancer (1984); 54 (11): 2450-2455.
Kawasaki, et al., "Presence of four major haplotypes in human BCMA gene: lack of association with systemic lupus erythematosus and rheumatoid arthritis," Genes and Immunity (2001); 2: 276-279.
Kohler, et al., "Continuous cultures of fused cells secreting antibody of predefined specificity," Nature (1975); 256: 495-497.
Kyle and Rajkumar, "Criteria for diagnosis, staging, risk stratification and response assessment of multiple myeloma." Leukemia (2009); 23(1): 3-9.
Kyle, Robert A., "The Monoclonal Gammopathies," Clinical Chemistry (1994); 40/11 (B): 2154-2161.
Laabi, et al., "A new gene, BCM, on chromosome 16 is fused to the interleukin 2 gene by a t(4;16)(q26;p13) translocation in a malignant T cell lymphoma," The EMBO Journal (1992); 11(11): 3897-3904.
Laabi, et al., "The BCMA gene, preferentially expressed during B lymphoid maturation, is bidirectionally transcribed," Nucleic Acids Research (1994); 22 (7): 1147-1154.
Laras, et al., "Substituted thiazolamide coupled to a redox delivery system: a new γ-secretase inhibitor with enhanced pharmacokinetic profile." Org. Biomol. Chem. (2005); 3: 612-618.
Laurent, et al., "γ-secretase directly sheds the survival receptor BCMA from plasma cells." Nature Communications (2015); 6: 7333, 12 pages.
Lee, et al., "Prognosis of Chronic Lymphocytic Leukemia: A Multivariate Regression Analysis of 325 Untreated Patients." Blood (1987); 69 (3): 929-936.
Li, et al., "The Pro-angiogenic Cytokine Pleiotrophin Potentiates Cardiomyocyte Apoptosis through Inhibition of Endogenous AKT/PKB Activity." The Journal of Biological Chemistry (2007); 282 (48): 34984-34993.
Liu, T., et al., "Interleukin-6 and JAK2/STAT3 signaling mediate the reversion of dexamethasone resistance after dexamethasone withdrawal in 7TD1 multiple myeloma cells." Leukemia Research (2013); 37(10): 1322- 1328.
Mackay, et al., "Mice Transgenic for BAFF Develop Lymphocytic Disorders Along with Autoimmune Manifestations," J. Exp. Med., 190(11):1697-1710 (1999).
Madry, et al., "The characterization of murine BCMA gene defines it as a new member of the tumor necrosis factor receptor superfamily," International Immunology (1998); 10(11): 1693-1702.
Marks, et al., "By-passing Immunization Human Antibodies from V-gene Libraries Displayed on Phage,"J. Mol. Biol., 222: 581-597 (1991).
McLendon, et al., "Cell-free assays for γ-secretase activity." The FASEB Journal (2000); 14 (15): 2383-2386.
Moreaux, et al., "BAFF and APRIL protect myeloma cells from apoptosis induced by interleukin 6 deprivation and dexamethasone." Blood (2004); 103(8): 3148-3157.
Morrison, et al., "Chimeric human antibody molecules: Mouse antigen-binding domains with human constant region domains." Proc. Natl. Acad. Sci. USA (1984); 81: 6851-6855.
Mukhopadhyay, et al., "Identification and Characterization of a Novel Cytokine, Thank, a TNF Homologue That Activates Apoptosis, Nuclear Factor-kB, and c-Jun NH2-Terminal Kinase." J. Biol. Chem. (1999); 274 (23): 15978-15981.
Muramatsu, T., "Midkine and Pleiotrophin: Two Related Proteins Involved in Development, Survival, Inflammation and Tumorigenesis." The Journal of Biochemistry (2002); 132 (3): 359-371.
Novak, et al., "Expression of BCMA, TACI, and BAFF-R in multiple myeloma: a mechanism for growth and survival." Blood (2004); 103 (2): 689-694.
Oki, et al., "Serum BLyS Level as a Prognostic Marker in Patients with Lymphoma." Blood (2005); ASH Annual Meeting Abstracts, 106(11): 1926.

Palumbo, A., et al., "Lenalidomide in combination with dexamethasone for the treatment of relapsed or refractory multiple myeloma." Blood Reviews (2009); 23 (2): 87-93.
Pemovska, T., et al., "Individualized Systems Medicine Strategy to Tailor Treatments for Patients with Chemorefractory Acute Myeloid Leukemia." Cancer Discovery (2013); 13 (12): 1416-1429.
Pemovska, T., et al., "Individualized Systems Medicine Strategy to Tailor Treatments for Patients with Chemorefractory Acute Myeloid Leukemia." Cancer Discovery (2013); 13 (12): 1416-1429; Supplementary Materials. DOI: 10.1158/2159-8290.CD-13-0350 URL:http://cancerdiscovery.aacrjournals.org/content/candisc/suppl/2013/09/18/2159-8290.CD-13-0350.DC1/supp_figs_tables_and_methods.pdf.
Ponticelli, et al., "Modulation of Angiogenesis by a Tetrameric Tripeptide That Antagonizes Vascular Endothelial Growth Factor Receptor." The Journal of Biological Chemistry (2008); 283 (49): 34250-34259.
Prasad, et al., Discovery of (S)-2-((S)-2-(3,5-difluorophenyl)-2-hydroxyacetamido)-N-((S,Z)-3-methyl-4-oxo- 4,5-dihydro-3Hbenzo[d][1,2]diazepin-5-yl)propanamide (BMS-433796): A γ-secretase inhibitor with Aß lowering activity in a transgenic mouse model of Alzheimer's disease Bioorganic & Medicinal Chemistry Letters (2007); 17: 4006-4011.
Presta, Leonard G., "Antibody engineering," Current Opinion in Structural Biology (1992); 2: 593-596.
Pufe, et al., "Expression of pleiotrophin, an embryonic growth and differentiation factor, in rheumatoid arthritis." Arthritis & Rheumatism (2003); 48 (3): 660-667.
Purdue et al., "Pre-diagnostic serum levels of cytokines and other immune markers and risk of non-Hodgkin lumphoma." Cancer Res. (2011); 71 (14): 4898-4907.
Quackenbush, John, "Microarray data normalization and transformation." Nature Genetics (2002); Supp. 32: 496-501.
Rajkumar, et al., "Consensus recommendations for the uniform reporting of clinical trials: report of the International Myeloma Workshop Consensus Panel 1." Blood (2011); 117 (18):4691-4695.
Rennert, et al., "A soluble Form of B Cell Maturation Antigen, a Receptor for the Tumor Necrosis Factor Family Member APRIL, Inhibits Tumor Cell Growth." J. Exp. Med. (2000); 192 (11): 1677-1683.
Riechmann et al., "Reshaping human antibodies for therapy," Nature (1988); 332: 323-327.
Rodwell and McKearn, "Linker Technology: Antibody-Mediated Delivery Systems." Biotechnology (1985); 3: 889-894.
Sanchez, et al., EMBASE Accession No. 0050990829, "Evaluation of serum B-cell maturation antigen in multiple myeloma." J. Clin. Oncology (2012); 30 (15): (Suppl. 1 ): Abs. No. e 18549), 2 pages.
Sanchez, et al., "Serum B-cell maturation antigen is elevated in multiple myeloma and correlates with disease status and survival," British Journal of Haematology (2012); 158 (6): 727-738.
Sanchez, et al., BIOSIS Accession No. 2013:233275, "Serum Levels of B-Cell Maturation Antigen Are Elevated in Multiple Myeloma Patients and Correlate with Disease Status and Overall Survival." Blood (2012); 120 (21): 4026.
Sarfati, et al., "Elevation of IgE-Binding Factors in Serum of Patients With B Cell-Derived Chronic Lymphocytic Leukemia," Blood (1988); 71 (1): 94-98.
Schneider, et al., "BAFF, a Novel Ligand of the Tumor Necrosis Factor Family, Stimulates B Cell Growth," J. Exp. Med. (1999); 189 (11): 1747-1756.
Seshasayee, et al., "Loss of TACI Causes Fatal Lymphoproliferation and Autoimmunity, Establishing TACI as an Inhibitory BLyS Receptor," Immunity (2003); 18: 279-288.
Sharada, et al., "Intravenous dexamethasone pulse therapy in diffuse systemic sclerosis. A randomized placebo-controlled study." Rheumatology International (1994); 14 (3): 91-94.
Shu, et al., "TALL-1 is a novel member of the TNF family that is down-regulated by mitogens," Journal of Leukocyte Biology (1999); 65 (5): 680-683.
Simonsson, et al., "b 2-Microglobulin in Chronic Lymphocytic Leukaemia." Scand J Haematol (1980); 24 (2): 174-180.
Slonim, Donna K., "From patterns to pathways: gene expression data analysis comes of age." (2002) Nature Genetics (2002); Suppl. 32: 502-508.

(56) References Cited

OTHER PUBLICATIONS

Smith, et al., "The TNF Receptor Superfamily of Cellular and Viral Proteins: Activation, Costimulation, and Death." Cell (1994); 76: 959-962.
Stephens, et al., "An intermediate-risk multiple myeloma subgroup is defined by sIL-6r: levels synergistically increase with incidence of SNP rs2228145 and 1q21 amplification." Blood (2012); 119 (2): 503-512.
The International Myeloma Working Group, "Criteria for the classification of monoclonal gammopathies, multiple myeloma and related disorders: a report of the International Myeloma Working Group." British Journal of Haematology (2003); 121 (5): 749-757.
Thompson, et al., "BAFF Binds to the Tumor Necrosis Factor Receptor-like Molecule B Cell Maturation Antigen and Is Important for Maintaining the Peripheral B Cell Population." J. Exp. Med. (2000); 192 (1): 129-135.
Thompson, et al., "BAFF-R, a Newly Identified TNF Receptor That Specifically Interacts with BAFF." Science (2001); 293: 2108-2111.
Van Oers, et al., "Expression and Release of CD27 in Human B-Cell Malignancies." Blood 82(11):3430-3436 (Dec. 1, 1993).
Varfolomeev, et al., "APRIL-Deficient Mice Have Normal Immune System Development." Molecular and Cellular Biology (2004); 24 (3): 997-1006.
Wu, et al., "Tumour Necrosis Factor (TNF) Receptor Superfamily Member TACI Is a High Affinity Receptor for TNF Family Members APRIL and BLyS." Journal of Biological Chemistry, 275(45):35478-35485 (2000).
Xu, et al., "B-Cell Maturation Protein, Which Binds the Tumour Necrosis Factor Family Members BAFF and APRIL, Is Dispensable for Humoral Immune Responses." Molecular and Cellular Biology (2001); 21 (12): 4067-4074.
Yan, et al., "Identification of a novel receptor for B lymphocyte stimulator that is mutated in a mouse strain with severe B cell deficiency." Current Biology (2001); 11: 1547-1552.
Yu, et al., "APRIL and TALL-1 and receptors BCMA and TACI: system for regulating humoral immunity." Nature Immunology (2000); 1 (3): 252-256.
Zhang, et al., "Cutting Edge: A Role for B Lymphocyte Stimulator in Systemic Lupus Erythematosus." The Journal of Immunology (2001); 166: 6-10.
Deshayes, et al., "Abnormal production of the TNF-homologue APRIL increases the proliferation of human malignant glioblastoma cell lines via a specific receptor." Oncogene (2004); 23 (17): 3005-3012.
EP Application No. 17738918.6, Extended European Search Report dated Jun. 6, 2019, 11 pages.
Ghermezi, et al., "Serum B-cell maturation antigen: a novel biomarker to predict outcomes for multiple myeloma patients." Haematologica (2017); 102 (4): 785-795. Epub Dec. 2, 20169.
International Preliminary Report on Patentability for International Application No. PCT/US2017/032894, dated Nov. 20, 2018, 6 pages.
International Search Report and Written Opinion for International Application No. PCT/US2018/037275, mailed Oct. 26, 2018, 15 pages.
Invitation to Pay Additional Fees for International Application No. PCT/US2014/015338, mailed Apr. 21, 2014, 2 pages.
Invitation to Pay Additional Fees for International Application No. PCT/US2018/037275, mailed Aug. 27, 2018, 2 pages.
Karpusas, et al., "Crystal structure of extracellular human BAFF, a TNF family member that stimulates B lymphocytes." Journal of Molecular Biology (2002); 315(5): 1145-1154.
O'Connor, et al., "BCMA Is Essential for the Survival of Long-lived Bone Marrow Plasma Cells". Journal of Experimental Medicine (2004); 199(1): 91-97.
Pelekanou, et al., "BAFF, APRIL, TWEAK, BCMA, TACI and Fn14 proteins are related to human glioma tumor grade: immunohistochemistry and public microarray data meta-analysis." PLoS One (2013); 8 (12):e83250, and Supplementary Data, Table S2, 12 pages.

Rihacek, et al., "B-Cell Activating Factor as a Cancer Biomarker and Its Implications in Cancer-Related Cachexia." Biomed Res Int. (2015); 2015: 792187. Epub Aug. 3, 2015.
Sanchez, et al., "Circulating Bcma Binding to Its Ligand BAFF Prevents Normal Antibody Production in Multiple Myeloma Patients." Blood (2014); 124: 4713.
Sanchez, et al., "Soluble B-Cell Maturation Antigen Mediates Tumor-Induced Immune Deficiency in Multiple Myeloma." Clin Cancer Res. (Jul. 2016); 22(13): 3383-3397. Epub Mar. 9, 2016.
Sanchez, et al., "Soluble Bcma in Myeloma Serum Binds Its Ligands BAFF and Prevents Normal Antibody Production in Multiple Myeloma Patients." Blood (2015); 126: 1799.
Bersenson, et al., "A Phase l Study of Ruxolitinib, Lenalidomide, and Steroids for Patients with Relapsed/Refractory Multiple Myeloma". Clin. Cancer Res. (May 2020); 26(10): 2346-2353. Epub Jan. 14, 2020.
Database Medline [Online] US National Library of Medicine (NLM), Bethesda, MD, US; Mar. 2016 (Mar. 2013), Abdelgawad, Iman A., et al., "Significance of Some Proliferation Markers and Some Prognostic Factors in Patients with Multiple Myeloma and their Impact on the Patients' Survival", Database accession No. NLM27268602 & Abdelgawad, et al., "Significance of Proliferation Markers and Prognostic Factors in Egyptian Patients with Multiple Myeloma". Asian Pac J Cancer Prev. (2016); 17(5): 2389-2394, 1 page.
Abdelgawad, et al., "Significance of Proliferation Markers and Prognostic Factors in Egyptian Patients with Multiple Myeloma". Asian Pacific Journal of Cancer Prevention (2016); 17(3): 1351-1355.
EP Application No. 17800006.3, Extended European Search Report dated Jun. 25, 2020, 16 pages.
EP Application No. 17800006.3, Partial Supplementary European Search Report dated Jan. 20, 2010, 17 pages.
Fragioudaki, et al., "B cell-activating factor: its clinical significance in multiple myeloma patients". Annals of Hematology (Sep. 2012); 91(9): 1413-1418. Epub Apr. 21, 2012.
Fragioudaki, et al., "Serum BAFF levels are related to angiogenesis and prognosis in patients with multiple myeloma". Leukemia Research (Aug. 2012); 36(8): 1004-1008. Epub Apr. 10, 2012.
Gabrilovic, et al., "Myeloid-derived suppressor cells". Cancer Immunol Res. (Jan. 2017); 5(1): 3-8.
Gu, et al., "Notch signaling: its roles and therapeutic potential in hematological malignancies". Oncotarget (May 17, 2016); 7(20): 29804-29823.
Holthof and Mutis, "Challenges for Immunotherapy in Multiple Myeloma: Bone Marrow Microenvironment-Mediated Immune Suppression and Immune Resistance". Cancers (Basel) (Apr. 17, 2020); 12(4): 988.
Kreuzaler, et al., "Soluble BAFF Levels Inversely Correlate with Peripheral B Cell Numbers and the Expression of BAFF Receptors". The Journal of Immunology (Jan. 1, 2012); 188(1): 497-503. Epub Nov. 28, 2011.
Lemancewicz, et al., "Evaluation of TNF superfamily molecules in multiple myeloma patients: Correlation with biological and clinical features", Leukemia Research (Sep. 2013); 37(9): 1089-1093. Epub Jun. 12, 2013.
Sanchez, Eric, "The clinical significance of B-cell maturation antigen as a therapeutic target and biomarker." Expert Rev Mol Diagn (Mar. 7, 2018); 18(4): 319-329.
Moir, Susan, "Decreased survival of B cells of HIV-viremic patients mediated by altered expression of receptors of the TNF superfamily". Journal of Experimental Medicine (2004); 200(5): 587-599.
Shaker, Olfat G, "Expression of TNF-α, April and BCMA in Behcet's Disease." Journal of Immunology Research (Nov. 5, 2014); vol. 2014, p. 380405.
Huntington, Nicholas D., "A Baff antagonist suppresses experimental autoimmune encephalomyelitis by targeting cell-mediated and humoral immune responses." International Immunology (Oct. 2006); 18(10): 1473-1485.
Maglione, Paul J., "Serum B-Cell Maturation Antigen (BCMA) Levels Differentiate Primary Antibody Deficiencies." Journal of Allergy and Clinical Immunology: In Practice (Jan. 2020); 8(1): 283-291.

(56) References Cited

OTHER PUBLICATIONS

Maglione, Paul J., "Reduced serum BCMA levels distinguish patients with primary antibody deficiency." Journal of Immunology (May 1, 2016); 196(Supp. 1), p. 193.7.
PCT/US2018/037275, International Preliminary Report on Patentability dated Dec. 17, 2019, 10 pages.
PCT/US2019/059199, International Search Report and Written Opinion mailed Jan. 14, 2020, 9 pages.
Picarda, et al., "Molecular Pathways: Targeting B7-H3 (CD276) for Human Cancer Immunotherapy". Clin Cancer Res. (Jul. 15, 2016); 22(14): 3425-3431. Epub May 20, 2016.
Rong, Jin, "Age-related changes in BAFF and APRIL profiles and upregulation of BAFF and APRIL expression in patients with primary antibody deficiency." Int J Mol Med (Feb. 2008); 21(2): 233-238.
Shih and Wang, "Notch Signaling, γ Secretase Inhibitors, and Cancer Therapy". Cancer Res (2007); 67(5): 1879-1882.
Syn, et al., "De-novo and acquired resistance to immune checkpoint targeting". Lancet Oncol. (Dec. 2017); 18(12): e731-e741.
Vardanyan, et al., "Serum Levels of B-Cell Maturation Antigen Are Elevated in Waldenström's Macroglobulinemia Patients and Correlate with Disease Status and Conventional M-Protein and IgM Levels". Blood Journal (Dec. 3, 2015); 126(23): 1778.
Zhang, et al., "B Cell-Activating Factor as a New Potential Marker in Inflammatory Bowel Disease". Digestive Diseases and Sciences (Sep. 2016); 61(9): 2608-2618. Epub Apr. 7, 2016.
Boasso, et al., "Immune dysregulation in human immunodeficiency virus infection: know it, fix it, prevent it", J Intern Med. (Jan. 2009); 265(1): 78-96.
Carbone, et al., "Potential role of serum BAFF as a biomarker in HIV infection", Infectious Diseases (2015); 47(4): 260-262. Epub Feb. 17, 2015.
EP Application No. 18818048.3, Extended European Search Report dated Mar. 17, 2021, 9 pages.
International Preliminary Report on Patentability for International Application No. PCT/US2019/059199, dated Apr. 27, 2021, 5 pages.
Rodriguez, et al., "Plasma levels of B-lymphocyte stimulator increase with HIV disease progression", AIDS (Sep. 5, 2003); 17(13): 1983-1985.
Torzewski, et al., "Animal Models of C-Reactive Protein", Mediators of Inflammation (2014); 2014: 683598, pp. 1-7.
Van Der Vekens, et al., "Human and equine cardiovascular endocrinology: beware to compare", Cardiovascular Endocrinology (Dec. 2013); 2(4): 67-76.
[Author Unknown] R&D Systems, Inc., "Quantikine ELISA Human CYR61/CCN1 Immunoassay", Catalog No. DCYR10 (2014), 16 pages.
Ali, et al., Abstract P1-02-10; "Reduced serum B-cell maturation antigen levels predict poor outcome in metastatic breast cancer patients in a phase 3 randomized 2nd-line hormone therapy trial". Presented at: San Antonio Breast Cancer Symposium; Dec. 6-10, 2016; San Antonio, TX, 1 page.
Bahadir and Sezgintürk, "Lateral flow assays: Principles, designs, and labels". Trends in Analytical Chemistry (2016);82: 286-306.
Dou, et al., "APRIL, BCMA and TACI proteins are abnormally expressed in non-small cell lung cancer". Oncol Lett. (Nov. 2016); 12(5): 3351-3355. Epub Sep. 6, 2016.
Tockman, et al., "Considerations in Bringing a Cancer Biomarker to Clinical Application". Cancer Research (May 1, 1992); 52(Suppl.): 2711s-2718s.
Byrne Michael et al., "Leveraging JAK-STAT regulation in myelofibrosis to improve outcomes with allogeneic hematopoietic stem-cell transplant", The Rapeutic Advances in Hematology, vol. 9, No. 9, Sep. 1, 2018 (Sep. 1, 2018 ), pp. 251-259, Retrieved from the Internet: URL:http://journals.sagepub.com/doi/full-XML/10.1177/2040620718786437.
Debureaux P. E., et al., "Nivolumab combined with ruxolitinib: antagonism or synergy", Annals of Oncology, vol. 29, No. 5, May 1, 2018 (May 1, 2018 ), pp. 1333-1334.
Jianxuan Zou et al., "Immunotherapy based on bispecific T-cell engager with hIgG1 Fe sequence as a new therapeutic strategy in multiple myeloma", Cancer Science, vol. 106, No. 5,Mar. 13, 2015 (Mar. 13, 2015), pp. 512-521.
Jin et al., "Age-related changes in BAFF and APRIL profiles and upregulation of BAFF and APRIL expression in patients with primary antibody deficiency," International J. Mol. Med., 2008, vol. 21, pp. 233-238.
Kenderian, S. S., et al., "Ruxolitinib Prevents Cytokine Release Syndrome after Car T-Cell Therapy Without Impairing the Anti-Tumor Effect in a Xenograft Model", Biology of Blood and Marrow Transplantation, vol. 23, No. 3, 2017, pp. S19-S20.
Ma Jing et al., "Immunotherapy Strategies Against Multiple Myeloma", Technology in Cancer Research and Treatment, vol. 16, No. 6, Dec. 1, 2017 (Dec. 1, 2017), pp. 717-726, Retrieved from the Internet: URL:https://www.ncbi.nlm.nih.gov/pmc/articles/PMC5762093/pdf/10.1177_1533034617743155.pdf.
Nijland Marcel et al., "Combined PD-1 and JAK1/2 inhibition in refractory primary mediastinal B-cell lymphoma" Annals of Hematology, Berlin, DE, vol. 97, No. 5, Jan. 11, 2018 (Jan. 11, 2018 ), pp. 905-907.
O'Farrell, Brendan, Evolution in Lateral Flow-based Immunoasssay Systems, Lateral Flow Immunoassay, 2008, Oct. 31; pp. 1-33 . (Year: 2008).
Salzer, U, et al., "Screening of functional and positional candidate genes in familieswith common variable immunodeficiency" BMC Immunology, 2008, vol. 9, 9 pages.
Tempfer, C. B., et al., "Thalidomide and lenalidomide for recurrent ovarian cancer: A systematic review of the literature", Oncology Letters, vol. 14, No. 3, Sep. 15, 2017 (Sep. 15, 2017), pp. 3327-3336.

\* cited by examiner

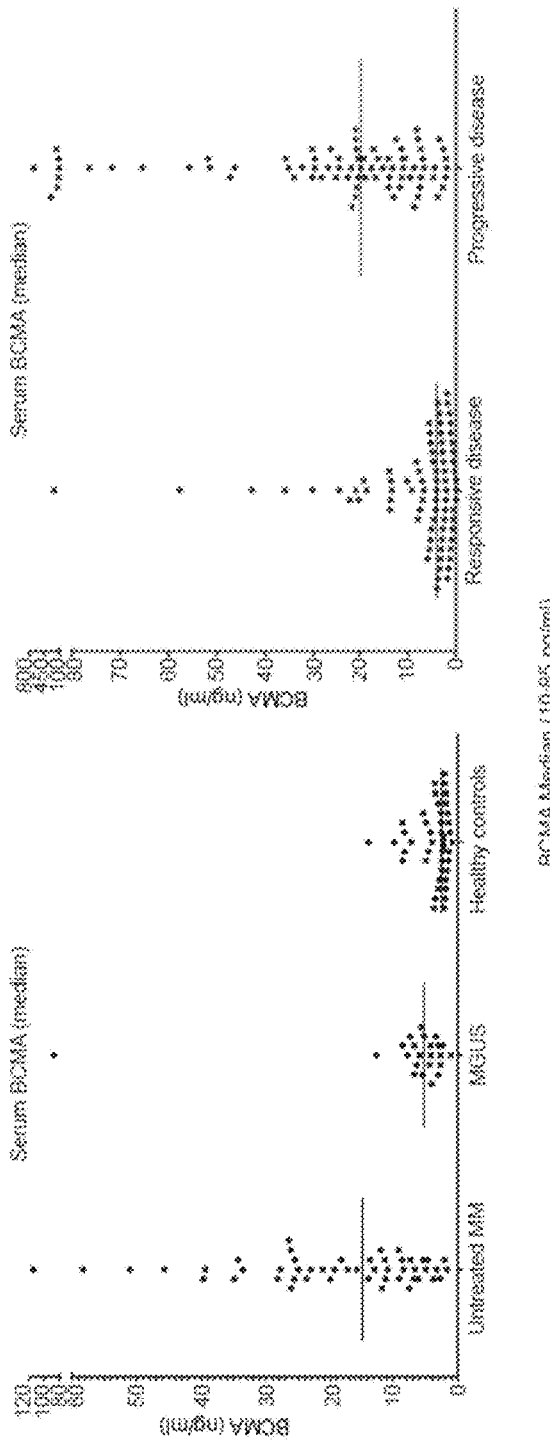
FIG. 3A
FIG. 3B
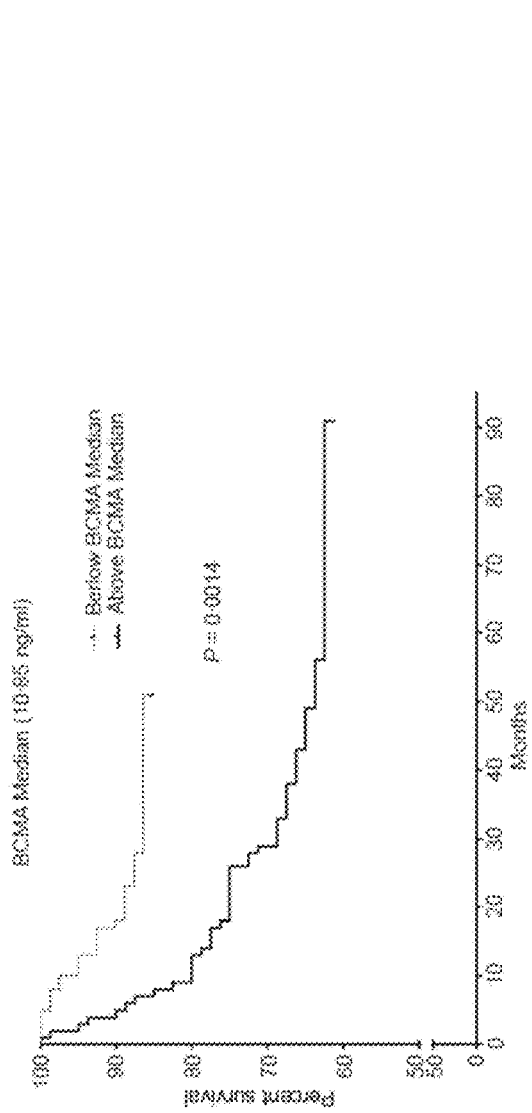
FIG. 3C

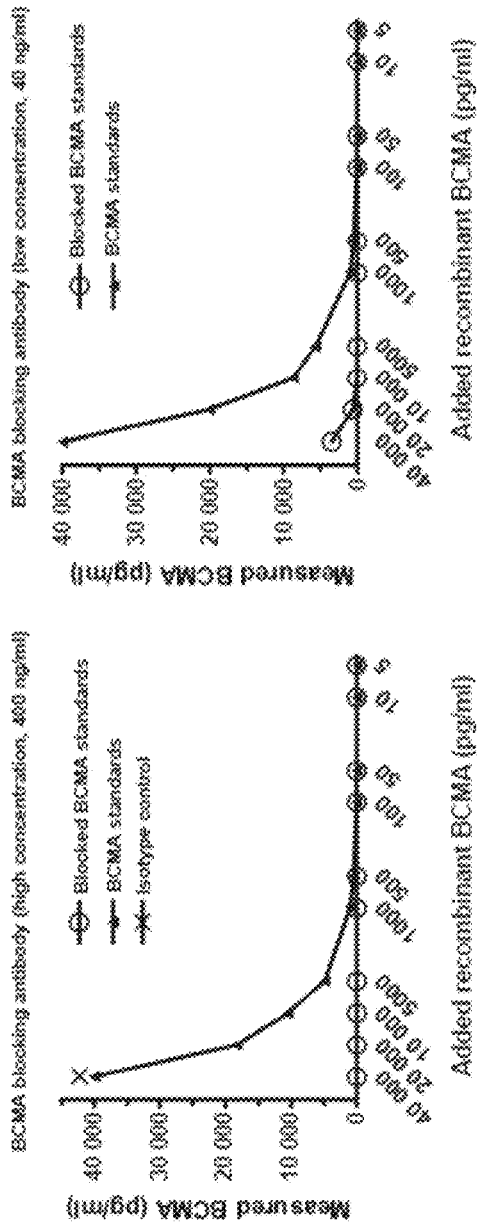
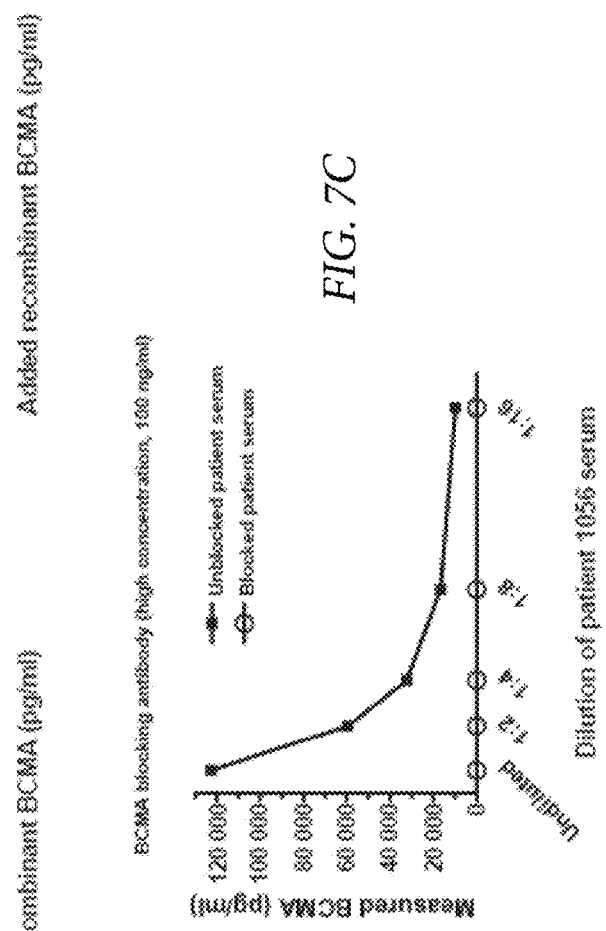
FIG. 7A
FIG. 7B
FIG. 7C

FIG. 9A
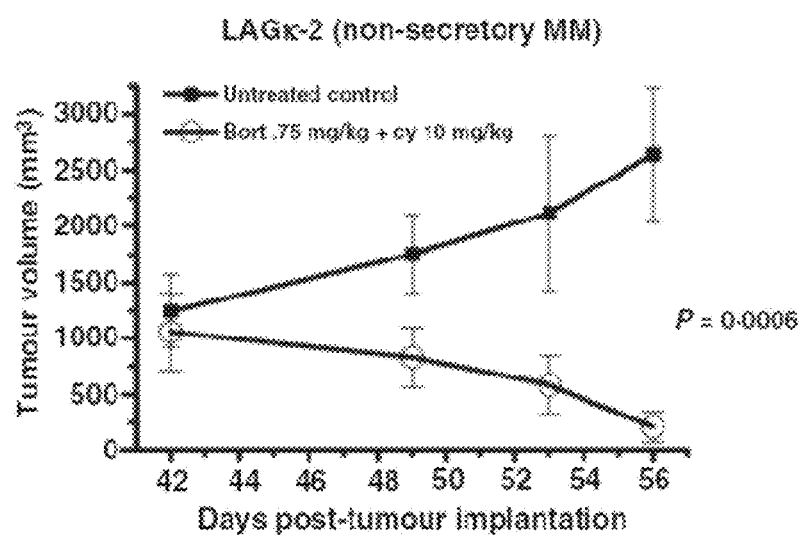
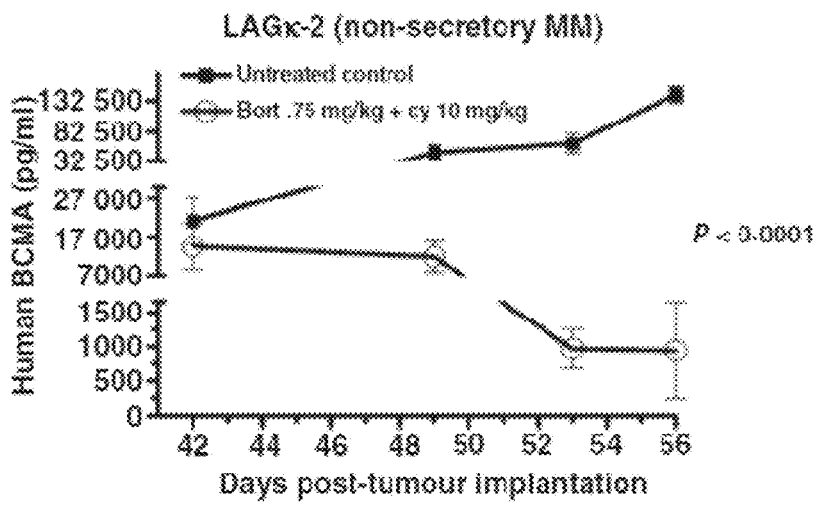
FIG. 9B

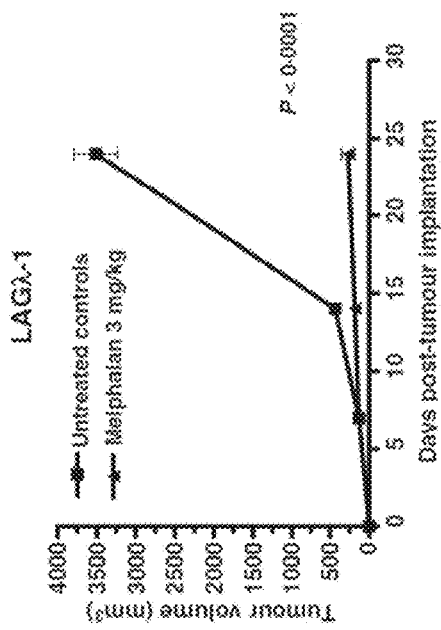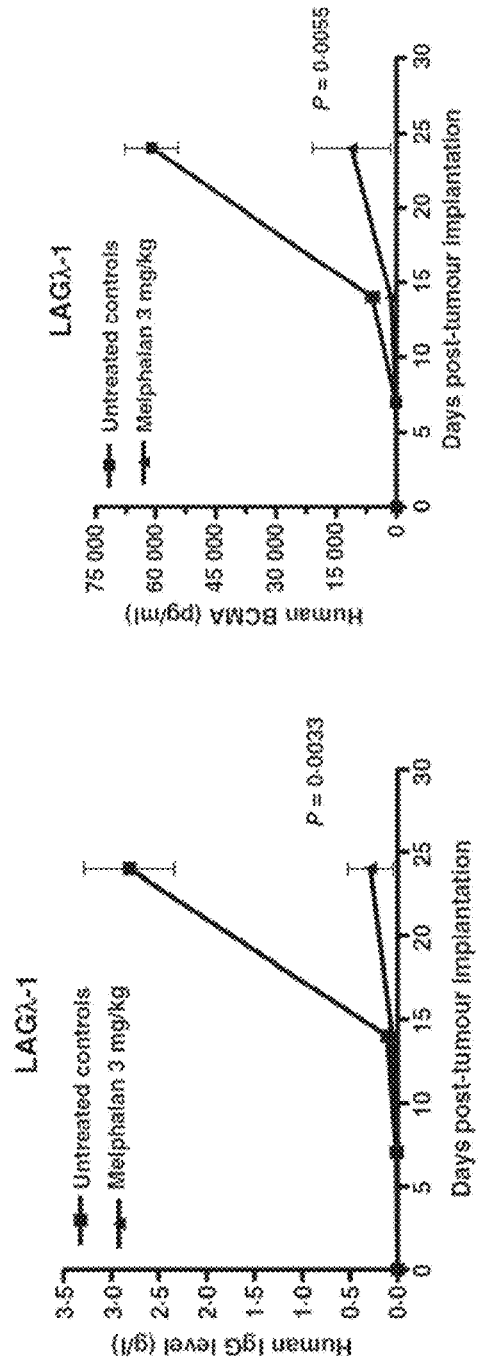
FIG. 10A
FIG. 10B
FIG. 10C

DIAGNOSTIC, PROGNOSTIC, AND MONITORING METHODS FOR CHRONIC LYMPHOCYTIC LEUKEMIA

CROSS-REFERENCE TO RELATED APPLICATIONS

This application is a divisional of U.S. application Ser. No. 14/766,694, issued as U.S. Pat. No. 10,126,301 on Nov. 13, 2018, which is the National Stage of International Application No. PCT/US2014/015338, filed Feb. 7, 2014, which claims the benefit under 35 U.S.C. § 119(e) of U.S. Provisional Patent Application No. 61/762,753, filed Feb. 8, 2013. The foregoing applications are incorporated herein by reference in their entirety.

BACKGROUND

Technical Field

The compositions and methods of the invention relate generally to detection of biomarkers for the diagnosis, prognosis, and monitoring of cancer. In particular, the invention relates to compositions and methods for detection of B-cell maturation antigen for the diagnosis, prognosis, and monitoring of multiple myeloma.

Description of the Related Art

Tumor necrosis factor receptor superfamily, member 17 (TNFRSF17, also designated as B-cell maturation antigen (BCMA) or CD269) is a receptor that was first identified in a T-cell tumor line (Laabi et al., 1992) and subsequently shown to be expressed in B lymphocytes as they mature (Laabi et al., 1994). BCMA ligands include BAFF (B cell-activating factor; TNFSF13B) and APRIL (a proliferation-inducing ligand; TNFSF13) (Rennert et al., 2000; Thompson et al., 2000). In multiple myeloma (MM) cell lines, these ligands activate cell proliferation pathways and upregulate anti-apoptotic proteins (Moreaux et al., 2004). Both ligands also bind the receptor TACI (transmembrane activator and CAML interactor; TNFRSF13B) (Gross et al., 2000; Wu et al., 2000; Yu et al., 2000). Additionally, BAFF binds to a third receptor, called BAFF-receptor (BAFFR; TNFRSF13C), whereas APRIL does not (Thompson et al., 2001; Day et al., 2005). The ligands BAFF and APRIL are members of the tumor necrosis family (TNF) and binding of TNF members to their receptors can lead to apoptosis, differentiation or proliferation (Smith et al., 1994). TNF family members act through autocrine, paracrine and endocrine mechanisms (Smith et al., 1994).

Transgenic mice that overexpress BAFF or are TACI-deficient display symptoms of systemic lupus erythematosus (SLE) and show B cell hyperplasia and increased levels of serum immunoglobulin (Ig) (McKay et al., 1999; Yan et al., 2001; Groom et al., 2002; Seshasayee et al., 2003). APRIL-deficient mice do not show B- or T-cell abnormalities (Varfolomeev et al, 2004). BCMA-deficient mice have normal peripheral B lymphocyte development, and their immune responses remain intact (Xu & Lam, 2001).

Serum BAFF levels are reported to be elevated in patients with autoimmune diseases and lymphoma (Cheema et al., 2001; Zhang et al., 2001; Oki et al., 2005). BCMA has been shown to be located intracellularly in plasma cell lines (Laabi et al., 1992, 1994). Surface expression of BCMA was found on human tonsilar B-cells (Thompson et al., 2000), and on human CD138-expressing MM cells (Novak et al., 2004). Malignant cells from Hodgkin lymphoma and Waldenstrom macroglobulinemia (WM) patients also express this protein (Elsawa et al., 2006; Chiu et al., 2007). However, serum levels of BCMA have not been previously reported in any disease.

Non-Hodgkin lymphoma (NHL) is a type of blood cancer that develops in the lymphatic system. The Leukemia and Lymphoma Society estimates that in 2011, about 502,943 people were living with NHL or are in remission (no sign of the disease). Like many other cancers, the incidence of NHL increases with age. The National Cancer Institute estimates that about 70,000 new cases will be diagnosed in 2012. Chronic lymphocytic leukemia (CLL) is the most common type of leukemia in adults. Children don't get CLL. The incidence of CLL increases significantly among people aged 50 years and older. A small number of adults are diagnosed in their 30s and 40s. The Leukemia and Lymphoma Society estimates that about 105,000 people were living with (or in remission from) CLL and about 14,500 people in the United States were diagnosed with CLL in 2011.

Multiple myeloma is also a prevalent blood cancer, representing approximately 1% of all cancers and 2% of all cancer deaths. Although the peak age of onset of multiple myeloma is 65 to 70 years of age, recent statistics indicate both increasing incidence and earlier age of onset. Approximately 100,000 Americans currently have myeloma, and the American Cancer Society estimates that approximately 22,000 new cases of myeloma are diagnosed each year in the United States.

B-cell maturation antigen is expressed on the surface of normal and malignant B-cells (Laabi et al., 1992, 1994; Thompson et al., 2000; Novak et al., 2004). Most cell surface markers used to diagnose MM, CLL, and NHL are not elevated or reliably expressed in a large segment of the relevant patient populations. For example, one surface receptor present on normal and malignant B-cells, the interleukin (IL)-6 receptor, has been shown to be elevated in the serum of MM patients (Jones et al., 2001) but only in approximately 15% of patients (Stephens et al., 2012). Some serum markers of CLL including $\beta_2$ microglobulin (Simonsson B et al., 1980), thymidine kinase (TK) (Kallander CFR et al., 1984), lactate dehydrogenase (LDH), (Lee J et al., 1987) soluble CD23 (Sarfati M et al., 1988), soluble CD27 (Van Oer's MHJ et al., 1993) and ICAM-I (Christiansen I et al., 1994) have reported to be positively correlated to clinical stage, but need to be further evaluated. A study was undertaken to assess the clinical significance of the serum molecules in NHL. The results showed CD23, CD27, CD30, or CXCL13 were at 2.8- to 5.5-fold increased risk in B-NHL and VEGF, and bFGF was found to be an important prognostic factor in B-NHL (Benboubker L et al 2000). Elevated levels of IL-10, TNF-α and sTNF-R1 sTNF-R2 were significantly associated with increased risk of NHL. (Purdue M. P. et al 2011). However, those molecules are not NHL specific diagnosis or prognosis markers.

Due to the difficulty in assessing the location of bone marrow (BM)-based malignancies and the heterogeneous involvement of malignant cells within different BM sites, measurement of MM, CLL, and NHL tumor mass is indirect; and, thus, response to therapy is often difficult to determine. Besides blood and urine monoclonal Ig levels, existing blood markers used to determine MM tumor mass include: hemoglobin, urea nitrogen, calcium, albumin, creatinine, monoclonal protein, beta-2 microglobulin (β2M), IL-6, C-reactive protein, soluble IL-6 receptor, lactate dehydrogenase, thymidine kinase, and al-antitrypsin (Kyle, 1994). However, these markers are not produced directly by MM cells and thus, are not reliable. In addition, existing markers are even less useful for monitoring the response of patients to treatment, probably due to their widespread presence in many other not malignant cell types (Jones et al., 2001). Thus, existing markers have not proven to be reliable diagnostics or predictors of response to anti-cancer treatments for MM, CLL and NHL (Kyle, 1994).

Accordingly, the art is deficient in reliable diagnostic, prognostic, and treatment monitoring biomarkers of multiple myeloma, chronic lymphocytic leukemia, and non-Hodgkin's lymphomas. In addition, existing biomarkers do not correlate well with response to anti-cancer treatment, or with the extent or severity of the disease.

BRIEF SUMMARY

The invention generally provides compositions and methods for reliably and reproducibly diagnosing and/or monitoring cancers such as multiple myeloma, chronic lymphocytic leukemia, and B-cell non-Hodgkin's lymphomas (NHL). The levels of BCMA and BAFF in the supernatants of cultured BMMCs and patient sera can be detected and/or measured and compared against a baseline or control to reliably and reproducibly diagnose and/or MM, CLL, or NHL in a subject.

In various embodiments, a method of diagnosing multiple myeloma (MM) is provided. In particular embodiments a method of diagnosing MM comprises: (a) detecting an amount of BCMA polypeptide or a fragment thereof in a biological sample obtained from a subject; and (b) comparing the amount of BCMA polypeptide or fragment thereof detected in step (a) to a predetermined cut-off value or to an amount detected in a control serum sample, wherein an increased amount of BCMA polypeptide or fragment in the biological sample of (a) as compared to the predetermined cut-off value or amount in the control serum sample of (b) indicates the presence of MM, wherein the biological sample is a serum sample or supernatant obtained from culture of the subject's bone marrow mononuclear cells or peripheral blood mononuclear cells.

In various embodiments, a method of diagnosing chronic lymphocytic leukemia (CLL) is provided. In particular embodiments, a method of diagnosing chronic CLL, comprises: (a) detecting an amount of BCMA polypeptide or a fragment thereof in a biological sample obtained from a subject; and (b) comparing the amount of BCMA polypeptide or fragment thereof detected in step (a) to a predetermined cut-off value or to an amount detected in a control serum sample, wherein an increased amount of BCMA polypeptide or fragment in the biological sample of (a) as compared to the predetermined cut-off value or amount in the control serum sample of (b) indicates the presence of CLL, wherein the biological sample is a serum sample or supernatant obtained from culture of the subject's bone marrow mononuclear cells or peripheral blood mononuclear cells.

In various embodiments, a method of diagnosing B-cell non-Hodgkin lymphoma (NHL) is provided. In certain embodiments, a method of diagnosing NHL, comprises: (a) detecting an amount of BCMA polypeptide or a fragment thereof in a biological sample obtained from a subject; and (b) comparing the amount of BCMA polypeptide or fragment thereof detected in step (a) to a predetermined cut-off value or to an amount detected in a control serum sample, wherein an increased amount of BCMA polypeptide or fragment in the biological sample of (a) as compared to the predetermined cut-off value or amount in the control serum sample of (b) indicates the presence of NHL, wherein the biological sample is a serum sample or supernatant obtained from culture of the subject's bone marrow mononuclear cells or peripheral blood mononuclear cells.

In particular embodiments, the biological sample is a serum sample. In certain embodiments, the biological sample is supernatant obtained from culture of the subject's bone marrow mononuclear cells. In certain particular embodiments, the biological sample is supernatant obtained from culture of the subject's peripheral blood mononuclear cells.

In certain embodiments, the BCMA fragment is a cleaved BCMA polypeptide.

In additional embodiments, the BCMA polypeptide or a fragment thereof is detected using a detection system selected from the group consisting of: an immunohistochemistry, enzyme-linked immunosorbent assay (ELISA), radioimmunoassay (RIA), enzyme immunoassay (EIA), fluorescence immunoassay (FIA), luminescence immunoassay (LIA), lateral flow assay, or strip assay. In further embodiments, the detection system is an ELISA assay. In some embodiments, the detection system is a lateral flow assay.

In particular embodiments, the detection is performed using an antibody specific for BCMA polypeptide or a fragment thereof. In certain embodiments, the antibody specific for BCMA polypeptide or a fragment thereof is a monoclonal antibody. In further embodiments, the antibody specific for BCMA polypeptide or a fragment thereof is a polyclonal antibody.

In various embodiments, a method of prognosis for the survival of a subject having or suspected of having multiple myeloma (MM) is provided. In certain embodiments, a method of prognosis for the survival of a subject having or suspected of having MM comprises: (a) detecting an amount of BCMA polypeptide or a fragment thereof in a biological sample obtained from a subject; and (b) comparing the amount of BCMA polypeptide or fragment thereof detected in step (a) to a the median value of levels of BCMA polypeptide or fragment thereof in a population of subj ects being treated for MM, wherein an increased amount of BCMA polypeptide or fragment thereof in the biological sample of (a) as compared to the median value or corresponding amount of BCMA polypeptide or fragment thereof in the treated population of (b) indicates a reduced chance of survival for the subject having MM, wherein the biological sample is a serum sample or supernatant obtained from culture of the subject's bone marrow mononuclear cells or peripheral blood mononuclear cells.

In various embodiments, a method of prognosis for the survival of a subject having or suspected of having chronic lymphocytic leukemia (CLL) is provided. In certain embodiments, a method of prognosis for the survival of a subject having or suspected of having CLL comprises: (a) detecting an amount of BCMA polypeptide or a fragment thereof in a biological sample obtained from a subject; and (b) comparing the amount of BCMA polypeptide or fragment thereof detected in step (a) to a the median value of levels of BCMA polypeptide or fragment thereof in a population of subj ects being treated for CLL, wherein an increased amount of BCMA polypeptide or fragment thereof in the biological sample of (a) as compared to the median value or corresponding amount of BCMA polypeptide or fragment thereof in the treated population of (b) indicates a reduced chance of survival for the subject having CLL, wherein the biological sample is a serum sample or supernatant obtained from culture of the subject's bone marrow mononuclear cells or peripheral blood mononuclear cells.

In various embodiments, a method of prognosis for the survival of a subject having or suspected of having B-cell non-Hodgkin lymphoma (NHL) is provided. In certain embodiments, a method of prognosis for the survival of a subject having or suspected of having NHL comprises: (a) detecting an amount of BCMA polypeptide or a fragment thereof in a biological sample obtained from a subject; and (b) comparing the amount of BCMA polypeptide or fragment thereof detected in step (a) to a the median value of levels of BCMA polypeptide or fragment thereof in a population of subjects being treated for NHL, wherein an increased amount of BCMA polypeptide or fragment thereof in the biological sample of (a) as compared to the median value or corresponding amount of BCMA polypeptide or fragment thereof in the treated population of (b) indicates a reduced chance of survival for the subject having NHL, wherein the biological sample is a serum sample or supernatant obtained from culture of the subject's bone marrow mononuclear cells or peripheral blood mononuclear cells.

In particular embodiments, the subject has been diagnosed with MM. In additional embodiments, the subject has received treatment for MM.

In certain embodiments, the subject has been diagnosed with CLL. In further embodiments, the subject has been diagnosed with CLL.

In some embodiments, the subject has been diagnosed with NHL. In related embodiments, the subject has been diagnosed with NHL.

In particular embodiments, the subject has a 10% reduction in the chance of survival compared to the survival of a subject having the median level of BCMA polypeptide. In certain embodiments, the subject has a 30% reduction in the chance of survival compared to the survival of a subject having the median level of BCMA polypeptide. In certain particular embodiments, the subject has a 50% reduction in the chance of survival compared to the survival of a subject having the median level of BCMA polypeptide. In other embodiments, the subject has a 70% reduction in the chance of survival compared to the survival of a subject having the median level of BCMA polypeptide.

In particular embodiments, the biological sample is a serum sample. In certain embodiments, the biological sample is supernatant obtained from culture of the subject's bone marrow mononuclear cells. In certain particular embodiments, the biological sample is supernatant obtained from culture of the subject's peripheral blood mononuclear cells.

In certain embodiments, the BCMA fragment is a cleaved BCMA polypeptide.

In additional embodiments, the BCMA polypeptide or a fragment thereof is detected using a detection system selected from the group consisting of: an immunohistochemistry, enzyme-linked immunosorbent assay (ELISA), radioimmunoassay (RIA), enzyme immunoassay (EIA), fluorescence immunoassay (FIA), luminescence immunoassay (LIA), lateral flow assay, or strip assay. In further embodiments, the detection system is an ELISA assay. In some embodiments, the detection system is a lateral flow assay.

In particular embodiments, the detection is performed using an antibody specific for BCMA polypeptide or a fragment thereof. In certain embodiments, the antibody specific for BCMA polypeptide or a fragment thereof is a monoclonal antibody. In further embodiments, the antibody specific for BCMA polypeptide or a fragment thereof is a polyclonal antibody.

In various embodiments, a method of monitoring the progression or response to treatment of multiple myeloma (MM) is provided. In particular embodiments, a method of monitoring the progression or response to treatment of MM, comprises: (a) detecting an amount of BCMA polypeptide or a fragment thereof in a biological sample obtained from a patient diagnosed with MM at a first time point; (b) detecting an amount of BCMA polypeptide or fragment thereof in a biological sample obtained from the patient at a second time point or following treatment; and (c) comparing the amount detected in step (a) to the amount detected in step (b), wherein an increased amount of BCMA polypeptide or a fragment thereof in the biological sample of (b) as compared to the amount of BCMA polypeptide or a fragment thereof in the biological sample of (b) indicates that said multiple myeloma is progressing, and wherein a decreased amount of BCMA polypeptide or a fragment thereof in the biological sample of (b) as compared to the amount in the biological sample of (a) indicates that said MM is entering remission or responding to treatment, wherein the biological sample is a serum sample or supernatant obtained from culture of the subject's bone marrow mononuclear cells or peripheral blood mononuclear cells.

In various embodiments, a method of monitoring the progression or response to treatment of chronic lymphocytic leukemia (CLL) is provided. In certain embodiments, a method of monitoring the progression or response to treatment of CLL, comprises: (a) detecting an amount of BCMA polypeptide or a fragment thereof in a biological sample obtained from a patient diagnosed with CLL at a first time point; (b) detecting an amount of BCMA polypeptide or fragment thereof in a biological sample obtained from the patient at a second time point or following treatment; and (c) comparing the amount detected in step (a) to the amount detected in step (b), wherein an increased amount of BCMA polypeptide or a fragment thereof in the biological sample of (b) as compared to the amount of BCMA polypeptide or a fragment thereof in the biological sample of (b) indicates that said CLL is progressing, and wherein a decreased amount of BCMA polypeptide or a fragment thereof in the biological sample of (b) as compared to the amount in the biological sample of (a) indicates that said CLL is entering remission or responding to treatment, wherein the biological sample is a serum sample or supernatant obtained from culture of the subject's bone marrow mononuclear cells or peripheral blood mononuclear cells.

In various embodiments, a method of monitoring the progression or response to treatment of B-cell non-Hodgkin lymphoma (NHL) is provided. In related embodiments, a method of monitoring the progression or response to treatment of NHL, comprises: (a) detecting an amount of BCMA polypeptide or a fragment thereof in a biological sample obtained from a patient diagnosed with NHL at a first time point; (b) detecting an amount of BCMA polypeptide or fragment thereof in a biological sample obtained from the patient at a second time point or following treatment; and (c) comparing the amount detected in step (a) to the amount detected in step (b), wherein an increased amount of BCMA polypeptide or a fragment thereof in the biological sample of (b) as compared to the amount of BCMA polypeptide or a fragment thereof in the biological sample of (b) indicates that said NHL is progressing, and wherein a decreased amount of BCMA polypeptide or a fragment thereof in the biological sample of (b) as compared to the amount in the biological sample of (a) indicates that said NHL is entering remission or responding to treatment, wherein the biological sample is a serum sample or supernatant obtained from culture of the subject's bone marrow mononuclear cells or peripheral blood mononuclear cells.

In particular embodiments, the biological sample is a serum sample. In certain embodiments, the biological sample is supernatant obtained from culture of the subject's bone marrow mononuclear cells. In certain particular embodiments, the biological sample is supernatant obtained from culture of the subject's peripheral blood mononuclear cells.

In certain embodiments, the BCMA fragment is a cleaved BCMA polypeptide.

In additional embodiments, the BCMA polypeptide or a fragment thereof is detected using a detection system selected from the group consisting of: an immunohistochemistry, enzyme-linked immunosorbent assay (ELISA), radioimmunoassay (RIA), enzyme immunoassay (EIA), fluorescence immunoassay (FIA), luminescence immunoassay (LIA), lateral flow assay, or strip assay. In further embodiments, the detection system is an ELISA assay. In some embodiments, the detection system is a lateral flow assay.

In particular embodiments, the detection is performed using an antibody specific for BCMA polypeptide or a fragment thereof. In certain embodiments, the antibody specific for BCMA polypeptide or a fragment thereof is a monoclonal antibody. In further embodiments, the antibody specific for BCMA polypeptide or a fragment thereof is a polyclonal antibody.

In various embodiments, a kit for detecting, diagnosing, predicting survival, staging, or monitoring multiple myeloma, chronic lymphocytic leukemia, or B-cell non-Hodgkin lymphoma in a patient is provided. In particular embodiments, a kit comprises a reagent suitable for determining levels of BCMA polypeptide or a fragment thereof in a biological sample obtained from a patient, wherein the biological sample is a serum sample or supernatant obtained from culture of the subject's bone marrow mononuclear cells or peripheral blood mononuclear cells.

In particular embodiments, a kit comprises an antibody specific for BCMA. In certain embodiments, a kit comprises an antibody specific for BCMA polypeptide or fragment thereof is a monoclonal antibody. In further embodiments, a kit comprises an antibody specific for BCMA polypeptide or fragment thereof is a polyclonal antibody.

In other embodiments, a kit comprises an ELISA assay. In other related embodiments, a kit comprises a lateral flow assay.

In various embodiments, a method of diagnosing multiple myeloma (MM), chronic lymphocytic leukemia (CLL), or B-cell non-Hodgkin lymphoma (NHL) is provided. In certain embodiments, the method comprises: (a) detecting an amount of BAFF polypeptide or a fragment thereof in a biological sample obtained from a subject; and (b) comparing the amount of BAFF polypeptide or fragment thereof detected in step (a) to a predetermined cut-off value or to an amount detected in a control serum sample, wherein an increased amount of BAFF polypeptide or fragment in the biological sample of (a) as compared to the predetermined cut-off value or amount in the control serum sample of (b) indicates the presence of MM, CLL, or NHL, wherein the biological sample is a serum sample or supernatant obtained from culture of the subject's bone marrow mononuclear cells or peripheral blood mononuclear cells.

In particular embodiments, the biological sample is a serum sample. In certain embodiments, the biological sample is supernatant obtained from culture of the subject's bone marrow mononuclear cells. In certain particular embodiments, the biological sample is supernatant obtained from culture of the subject's peripheral blood mononuclear cells.

In certain embodiments, the BAFF fragment is a cleaved BAFF polypeptide.

In additional embodiments, the BAFF polypeptide or a fragment thereof is detected using a detection system selected from the group consisting of: an immunohistochemistry, enzyme-linked immunosorbent assay (ELISA), radioimmunoassay (RIA), enzyme immunoassay (EIA), fluorescence immunoassay (FIA), luminescence immunoassay (LIA), lateral flow assay, or strip assay. In further embodiments, the detection system is an ELISA assay. In some embodiments, the detection system is a lateral flow assay.

In particular embodiments, the detection is performed using an antibody specific for BAFF polypeptide or a fragment thereof. In certain embodiments, the antibody specific for BAFF polypeptide or a fragment thereof is a monoclonal antibody. In further embodiments, the antibody specific for BAFF polypeptide or a fragment thereof is a polyclonal antibody.

In various embodiments, a method of prognosis for the survival of a subject having or suspected of having multiple myeloma (MM), chronic lymphocytic leukemia (CLL), or B-cell non-Hodgkin lymphoma (NHL) is provided. In particular embodiments, the method comprises: (a) detecting an amount of BAFF polypeptide or a fragment thereof in a biological sample obtained from a subject; and (b) comparing the amount of BAFF polypeptide or fragment thereof detected in step (a) to a median value of levels of BAFF polypeptide or fragment thereof in a population of subjects being treated for MM, CLL, or NHL wherein an increased amount of BAFF polypeptide or fragment thereof in the biological sample of (a) as compared to the median value or corresponding amount of BAFF polypeptide or fragment thereof in the treated population of (b) indicates a reduced chance of survival for the subject having MM, CLL, or NHL, wherein the biological sample is a serum sample or supernatant obtained from culture of the subject's bone marrow mononuclear cells or peripheral blood mononuclear cells.

In particular embodiments, the subject has been diagnosed with MM. In additional embodiments, the subject has received treatment for MM.

In certain embodiments, the subject has been diagnosed with CLL. In further embodiments, the subject has been diagnosed with CLL.

In some embodiments, the subject has been diagnosed with NHL. In related embodiments, the subject has been diagnosed with NHL.

In particular embodiments, the subject has a 10% reduction in the chance of survival compared to the survival of a subject having the median level of BAFF polypeptide. In certain embodiments, the subject has a 30% reduction in the chance of survival compared to the survival of a subject having the median level of BAFF polypeptide. In certain particular embodiments, the subject has a 50% reduction in the chance of survival compared to the survival of a subject having the median level of BAFF polypeptide. In other embodiments, the subject has a 70% reduction in the chance of survival compared to the survival of a subject having the median level of BAFF polypeptide.

In particular embodiments, the biological sample is a serum sample. In certain embodiments, the biological sample is supernatant obtained from culture of the subject's bone marrow mononuclear cells. In certain particular embodiments, the biological sample is supernatant obtained from culture of the subject's peripheral blood mononuclear cells.

In certain embodiments, the BAFF fragment is a cleaved BAFF polypeptide.

In additional embodiments, the BAFF polypeptide or a fragment thereof is detected using a detection system selected from the group consisting of: an immunohistochemistry, enzyme-linked immunosorbent assay (ELISA), radio-immunoassay (RIA), enzyme immunoassay (EIA), fluorescence immunoassay (FIA), luminescence immunoassay (LIA), lateral flow assay, or strip assay. In further embodiments, the detection system is an ELISA assay. In some embodiments, the detection system is a lateral flow assay.

In particular embodiments, the detection is performed using an antibody specific for BAFF polypeptide or a fragment thereof. In certain embodiments, the antibody specific for BAFF polypeptide or a fragment thereof is a monoclonal antibody. In further embodiments, the antibody specific for BAFF polypeptide or a fragment thereof is a polyclonal antibody.

In various embodiments, a method of monitoring the progression or response to treatment of multiple myeloma (MM), chronic lymphocytic leukemia (CLL), or B-cell non-Hodgkin lymphoma (NHL) is provided. In certain embodiments, the method comprises: (a) detecting an amount of BAFF polypeptide or a fragment thereof in a biological sample obtained from a patient diagnosed with MM, CLL, or NHL at a first time point; (b) detecting an amount of BAFF polypeptide or fragment thereof in a biological sample obtained from the patient at a second time point or following treatment; and (c) comparing the amount detected in step (a) to the amount detected in step (b), wherein an increased amount of BAFF polypeptide or a fragment thereof in the biological sample of (b) as compared to the amount of BAFF polypeptide or a fragment thereof in the biological sample of (a) indicates that said multiple myeloma is progressing, and wherein a decreased amount of BAFF polypeptide or a fragment thereof in the biological sample of (b) as compared to the amount in the biological sample of (a) indicates that said MM, CLL, or NHL is entering remission or responding to treatment, wherein the biological sample is a serum sample or supernatant obtained from culture of the subject's bone marrow mononuclear cells or peripheral blood mononuclear cells.

In particular embodiments, the biological sample is a serum sample. In certain embodiments, the biological sample is supernatant obtained from culture of the subject's bone marrow mononuclear cells. In certain particular embodiments, the biological sample is supernatant obtained from culture of the subject's peripheral blood mononuclear cells.

In certain embodiments, the BAFF fragment is a cleaved BAFF polypeptide.

In additional embodiments, the BAFF polypeptide or a fragment thereof is detected using a detection system selected from the group consisting of: an immunohistochemistry, enzyme-linked immunosorbent assay (ELISA), radio-immunoassay (RIA), enzyme immunoassay (EIA), fluorescence immunoassay (FIA), luminescence immunoassay (LIA), lateral flow assay, or strip assay. In further embodiments, the detection system is an ELISA assay. In some embodiments, the detection system is a lateral flow assay.

In particular embodiments, the detection is performed using an antibody specific for BAFF polypeptide or a fragment thereof. In certain embodiments, the antibody specific for BAFF polypeptide or a fragment thereof is a monoclonal antibody. In further embodiments, the antibody specific for BAFF polypeptide or a fragment thereof is a polyclonal antibody.

In various embodiments, a kit for detecting, diagnosing, predicting survival, staging, or monitoring multiple myeloma, chronic lymphocytic leukemia, or B-cell non-Hodgkin lymphoma in a patient is provided. In particular embodiments, a kit comprises a reagent suitable for determining levels of BAFF polypeptide or a fragment thereof in a biological sample obtained from a patient, wherein the biological sample is a serum sample or supernatant obtained from culture of the subject's bone marrow mononuclear cells or peripheral blood mononuclear cells.

In certain embodiments, the kit comprises an antibody specific for BAFF. In other embodiments, the kit comprises an antibody specific for BAFF polypeptide or fragment thereof is a monoclonal antibody. In related embodiments, the kit comprises an antibody specific for BAFF polypeptide or fragment thereof is a polyclonal antibody.

In other embodiments, the kit comprises an ELISA assay. In further embodiments, the kit comprises a lateral flow assay.

BRIEF DESCRIPTION OF THE SEVERAL VIEWS OF THE DRAWINGS

In FIG. 2A, BMMCs were cultured for 72 h, supernatants collected, and a BCMA ELISA performed. Patients with active MM had markedly higher BCMA levels than those with indolent multiple myeloma (MM), monoclonal gammopathy of undetermined significance (MGUS) or healthy controls. In FIG. 2B, patients with a high percentage of malignant cells, determined by light chain staining, demonstrated high concentrations of BCMA in their culture medium whereas those with few light-chain restricted cells had low BCMA levels in their culture medium (original magnification 9100). Data graphed are the mean±standard error of the mean using three replicates.

FIGS. 3A-3B show that soluble BCMA is found in the serum of MM patients and correlates with disease status and overall survival. In FIG. 3A, untreated multiple myeloma (MM) patients had significantly higher serum BCMA levels compared to monoclonal gammopathy of undetermined significance (MGUS) patients and normal controls (P=0.0157, P<0.0001, respectively). In FIG. 3B, serum BCMA levels from responding patients were lower compared to patients with progressive disease (P=0.0038). In FIG. 3C, Kaplan-Meier overall survival of MM patients with BCMA levels above the median (10.85 ng/mL) showed shortened survival compared to those with amounts below the median. Individual patients with multiple BCMA levels were analyzed from the time of their first assessment. Data graphed are of samples run in triplicates and are presented as medians.

FIG. 5I), the serum BCMA level of an untreated MM patient was found to decrease after the individual achieved a partial response (PR) or complete response (CR). The serum BCMA level of patients increased when they developed progressive disease (PD).

FIGS. 7A-7G shows that polyclonal blocking and monoclonal anti-BCMA antibodies (Abs) confirm the presence of BCMA in MM serum. BCMA standards were undetectable when incubated with a polyclonal anti-BCMA Ab (FIG. 7A). An isotype-matched control goat Ab (at the same high concentration) or BCMA standards incubated without the blocking polyclonal anti-BCMA Ab, did not have any impact on detection of BCMA (FIG. 7A). When the blocking polyclonal anti-BCMA Ab was used at a 10-fold lower concentration, only the high-concentration BCMA standards were detectable (FIG. 7B). BCMA was detected when BCMA standards were not incubated with the polyclonal anti-BCMA Ab (right panel). In FIG. 7C, polyclonal anti-BCMA Ab (100 ng/mL) blocked BCMA from undiluted and diluted (up to 1:16) serum of MM Patient 1056. In contrast, serum from the same patient in the absence of the blocking antibody detected BCMA, which decreased with serial dilution. A monoclonal anti-BCMA Ab detected the BCMA standards (FIG. 7E), and the pattern of levels was similar to those obtained when using the polyclonal anti-BCMA Ab (FIG. 7D). The pattern of BCMA levels from MM patients who were untreated (1429), in VGPR (1764) or CR (1004) or an MGUS individual (1725) using the polyclonal Ab (FIG. 7F) showed similar patterns of the results obtained with the monoclonal Ab (FIG. 7G).

FIGS. 9A-9B shows that BCMA is produced by live MM cells growing in tumor-bearing mice. To determine if the observed serum BCMA was the result of membrane-bound BCMA from dead MM cells, mice bearing 1000 mm³ LAGκ-2 tumors were dosed with bortezomib (bort) at 0.75 mg/kg plus cyclophosphamide (cy) at 10 mg/kg. Twelve hours following treatment, human BCMA levels were determined. Tumor volumes of LAGκ-2-bearing mice were markedly smaller (FIG. 9A; P=0.0006) when compared to untreated mice. Serum BCMA levels in LAGκ-2-bearing mice were also markedly lower (FIG. 9B; P<0.0001) when compared to untreated mice.

FIGS. 10A-10C shows that severe combined immunodeficient (SCID) mice bearing the LAGλ-1 MM tumor and treated with melphalan have a significant reduction in tumor size, IgG levels, and serum human BCMA levels. Mice bearing this human MM xenograft model, that shows secretory disease of IgGλ type, were dosed with melphalan (3 mg/kg) twice weekly via i.p. injection. Untreated SCID mice (n=4) had large tumor volumes whereas melphalan-treated mice (n=7) had small tumor volumes (FIG. 10A; P<0.0001). Levels of serum IgG were significantly reduced among drug-treated mice when compared to controls (FIG. 10B; P=0.0033). Levels of serum BCMA were significantly reduced among drug-treated mice when compared to controls (FIG. 10C; P=0.0055). Results presented are group means±standard error of the mean.

DETAILED DESCRIPTION

A. Overview

Figure 1:
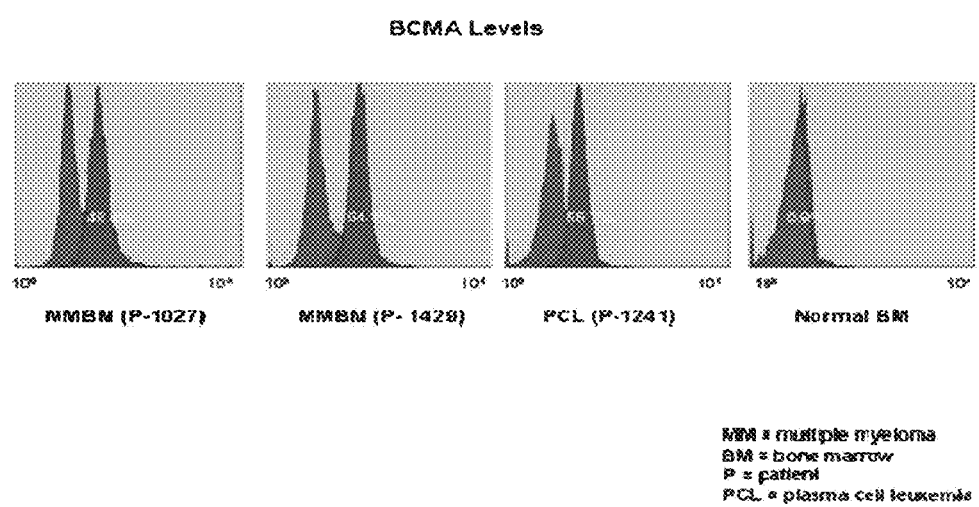
FIG. 1 shows flow cytometric analysis for detection of membrane bound BCMA in BM mononuclear cells (MCs). BMMCs were incubated overnight at 4° C. with goat anti-human BCMA Ab (R&D Systems) or control goat IgG (R&D Systems). The cells were washed and rabbit anti-goat Ab conjugated with FITC to detect BCMA were added to the samples (2 hours). The cells were washed and flow cytometric analysis completed using a Beckman Coulter FC500 cytometer with Cytomics CXP software (Beckman Coulter, Fullerton, CA). Statistical analysis of flow cytometric results was completed on the proportion of cells expressing BCMA using Cytomics CXP software.

Although BCMA is expressed on tumor cells in B-cell malignancies, it has not been found in serum. The present inventors have demonstrated that BCMA is present in the serum of patients having various B-cell malignancies, e.g., multiple myeloma (MM), chronic lymphocytic leukemia (CLL), and B-cell non-Hodgkin's lymphomas (NHL) and correlates with the patient's response to therapy and overall survival. In addition, the inventors have surprisingly discovered that levels of detectable BAFF are low in serum of MM, CLL, and NHL patients compared BAFF levels in non-diseased subjects, where those skilled in the art have reported detecting higher BAFF levels in serum.

In various embodiments, compositions and methods for reliably diagnosing multiple myeloma, chronic lymphocytic leukemia, and B-cell non-Hodgkin's lymphomas (NHL) are provided. BCMA and BAFF concentrations in the supernatants of cultured BMMCs and patient sera is detected and/or measured and compared against a baseline or control to reliably diagnose MM, CLL, or NHL in a subject. Without wishing to be bound to a particular theory, it is believed that because high serum BCMA levels were detected in MM, CLL, and NHL patients having active disease compared to patients having indolent disease, MGUS, or healthy subjects (not having MM), serum BCMA can be used to reliably diagnose MM, CLL, or NHL. Likewise, low serum levels of BAFF in patients having active disease compared to patients having indolent disease, MGUS, or healthy subjects can be used to reliably diagnose MM, CLL, or NHL.

Serum BCMA and BAFF concentrations can also be used for prognostic purposes, in determining the likelihood of survival of a subject having MM, CLL, or NHL or response of a subject to anti-MM, anti-CLL, or anti-NHL treatment. Without wishing to be bound to a particular theory, it is believed that because high serum BCMA levels were detected in MM, CLL, and NHL patients having progressive disease compared to patients having responsive disease and because patients having serum BCMA levels above the median of the population have overall shorter survival rates, serum BCMA can be used to reliably determine the survival of patients diagnosed with MM, CLL, or NHL. Similarly, it is believed that because low serum BAFF levels were detected in MM, CLL and NHL patients having progressive disease compared to patients having responsive disease and because patients having serum BAFF levels below the median of the population have overall shorter survival rates, serum BAFF can be used to reliably determine the survival of patients diagnosed with MM, CLL, or NHL In addition, BCMA and BAFF serum levels can be used to monitor the severity or extent of MM, CLL or NHL in the subject. Without wishing to be bound to a particular theory, it is believed that because high serum BCMA levels were detected in human MM, CLL and NHL xenografts and serum BCMA levels correlated with the change in tumor volume in response to anti-MM, anti-CLL, or anti-NHL agents, serum BCMA levels can be used as an efficient biomarker for monitoring disease status and overall survival of MM, CLL, and NHL patients.

The practice of the invention will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See, e.g., Sambrook, et al., *Molecular Cloning: A Laboratory Manual* (3rd Edition, 2001); Sambrook, et al., *Molecular Cloning: A Laboratory Manual* (2nd Edition, 1989); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford, 1985); Anand, *Techniques for the Analysis of Complex Genomes*, (Academic Press, New York, 1992); *Transcription and Translation* (B. Hames & S. Higgins, Eds., 1984); Perbal, *A Practical Guide to Molecular Cloning* (1984); and Harlow and Lane, Antibodies, (Cold Spring Harbor Laboratory Press, Cold Spring Harbor, N.Y., 1998).

All publications, patents and patent applications cited herein are hereby incorporated by reference in their entirety.

B. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred embodiments of compositions, methods and materials are described herein. For the purposes of the present invention, the following terms are defined below.

The articles "a," "an," and "the" are used herein to refer to one or to more than one (i.e., to at least one) of the grammatical object of the article. By way of example, "an element" means one element or more than one element.

As used herein, the term "about" or "approximately" refers to a quantity, level, value, number, frequency, percentage, dimension, size, amount, weight or length that varies by as much as 30, 25, 20, 25, 10, 9, 8, 7, 6, 5, 4, 3, 2, or 1% to a reference quantity, level, value, number, frequency, percentage, dimension, size, amount, weight or length. In particular embodiments, the terms "about" or "approximately" when preceding a numerical value indicates the value plus or minus a range of 15%, 10%, 5%, or 1%.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements Reference throughout this specification to "one embodiment," "an embodiment," "another embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "BCMA" is intended to generically refer to both the wild-type and variant B-cell maturation antigen polypeptides, unless specifically denoted otherwise. BCMA polypeptides are encoded by the BCMA gene. As it is commonly used in the art, the term "gene" is intended to refer to the genomic region encompassing 5' untranslated region(s) (UTR), exons, introns, and 3' UTR. Individual segments may be specifically referred to, e.g., promoter, coding region, etc. Combinations of such segments that provide for a complete BCMA protein may be referred to generically as a protein coding sequence. There are four major haplotypes of the BCMA gene in the human genome, in the present disclosure the term "BCMA" is meant to encompass all four (Kawasaki et al., Genes Immun. 2:276-9, 2001).

The term "BCMA polypeptide" encompasses an amino acid sequence encoded by an open reading frame (ORF) of a known BCMA polynucleotide, including the full-length native polypeptide and fragments thereof, particularly biologically active fragments and/or fragments corresponding to functional domains, e.g., a region or domain having biological activity, etc.; antigenic fragments thereof, and including fusions of the subject polypeptides to other proteins or parts thereof. The amino acid sequences of BCMA polypeptides have been disclosed. (See e.g., Laabi et al., *Nucleic Acids Research* 22: 1147-1154, 1994; Laabi et al., *EMBO J.*, 11: 3897-3904 (1992); Gras et al., *Int. Immunology*, 7: 1093-1106 (1995); and Madry et al., *Int. Immunology*, 10: 1693-1702 (1998). The BCMA polypeptides of the invention can be isolated from a variety of sources, such as from human tissue types or biological samples such as serum, bone, marrow, or tissue.

As used herein, the term "BAFF" refers to B-cell activating factor. BAFF is also known as tumor necrosis factor ligand superfamily member 13B, B Lymphocyte Stimulator (BLyS), TNF- and APOL-related leukocyte expressed ligand (TALL-1), and CD257. The term "BAFF" is intended to generically refer to both the wild-type and variant polypeptides, unless specifically denoted otherwise. BAFF polypeptides are encoded by the BAFF gene. As it is commonly used in the art, the term "gene" is intended to refer to the genomic region encompassing 5' untranslated region(s) (UTR), exons, introns, and 3' UTR. Individual segments may be specifically referred to, e.g., promoter, coding region, etc. Combinations of such segments that provide for a complete BAFF protein may be referred to generically as a protein coding sequence.

The term "BAFF polypeptide" encompasses an amino acid sequence encoded by an open reading frame (ORF) of a known BAFF polynucleotide, including the full-length native polypeptide and fragments thereof, particularly biologically active fragments and/or fragments corresponding to functional domains, e.g., a region or domain having biological activity, etc.; antigenic fragments thereof, and including fusions of the subject polypeptides to other proteins or parts thereof. The amino acid sequences of BAFF polypeptides have been disclosed. (See e.g., Schneider et al., *J Exp. Med.* 189 (11), 1747-1756 (1999); Mukhopadhyay et al., *J. Biol. Chem.* 274 (23), 15978-15981 (1999); Shu et al., *J. Leukoc. Biol.* 65 (5), 680-683 (1999)). The BAFF polypeptides of the invention can be isolated from a variety of sources, such as from human tissue types or biological samples such as serum, bone, marrow, or tissue. The terms "polynucleotide" and "nucleic acid molecule" are used interchangeably herein to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes single- and double-stranded and triple helical molecules. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as oligomers or oligos and may be isolated from genes, or chemically synthesized by methods known in the art.

The following are non-limiting embodiments of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A nucleic acid molecule may also comprise modified nucleic acid molecules, such as methylated nucleic acid molecules and nucleic acid molecule analogs. Analogs of purines and pyrimidines are known in the art. Nucleic acids may be naturally occurring, e.g., DNA or RNA, or may be synthetic analogs, as known in the art. Such analogs may be preferred for use as probes because of superior stability under assay conditions. Modifications in the native structure, including alterations in the backbone, sugars or heterocyclic bases, have been shown to increase intracellular stability and binding affinity. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. In various embodiments, BCMA polypeptides are contemplated for use within diagnostic, prognostic, or monitoring compositions and methods disclosed herein. The term includes fusion proteins, including, but not limited to, fusion proteins with a heterologous amino acid sequence, fusions with heterologous and homologous leader sequences, with or without N-terminal methionine residues; immunologically tagged proteins; and the like.

A "substantially isolated" or "isolated" substance is one that is substantially free of its associated surrounding materials in nature. By substantially free is meant at least 50%, preferably at least 70%, more preferably at least 80%, and even more preferably at least 90% free of the materials with which it is associated in nature. As used herein, an "isolated" can refer to polynucleotides, polypeptides, cells, samples, and antibodies.

Hybridization reactions can be performed under conditions of different "stringency". Conditions that increase stringency of a hybridization reaction are widely known and published in the art. See, for example, Sambrook et al. (1989). Examples of relevant conditions include (in order of increasing stringency): incubation temperatures of 25° C., 37° C., 50° C. and 68° C.; buffer concentrations of 10×SSC, 6×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water. Examples of stringent conditions are hybridization and washing at 50° C. or higher and in 0.1×SSC (9 mM NaCl/0.9 mM sodium citrate).

The term "target cell" includes an individual cell, cell from a biological sample, or cell culture. Target cells include progeny of a single target cell, and the progeny may not necessarily be completely identical (in morphology or in total DNA complement) to the original parent cell due to natural, accidental, or deliberate mutation and/or change. In particular embodiments, target cells include multiple myeloma cells, bone marrow or peripheral blood mononuclear cells or plasma-B cells.

Multiple myeloma is a B-cell malignancy of mature plasma cell morphology characterized by the neoplastic transformation of a single clone of these types of cells. These plasma cells proliferate in BM and may invade adjacent bone and sometimes the blood. Variant forms of multiple myeloma include overt multiple myeloma, smoldering multiple myeloma, plasma cell leukemia, non-secretory myeloma, IgD myeloma, osteosclerotic myeloma, solitary plasmacytoma of bone, and extramedullary plasmacytoma (see, for example, Braunwald, et al. (eds), *Harrison's Principles ofInternal Medicine,* 15th Edition (McGraw-Hill 2001)).

Chronic lymphocytic leukemia (CLL) is an indolent (slow-growing) cancer that causes a slow increase in immature white blood cells called B lymphocytes, or B cells. Cancer cells spread through the blood and bone marrow, and can also affect the lymph nodes or other organs such as the liver and spleen. CLL eventually causes the bone marrow to fail. Sometimes, the disease is called small lymphocytic lymphoma.

Non-Hodgkin lymphoma encompasses a large group of cancers of lymphocytes (white blood cells). These types of lymphomas can occur at any age and are often marked by lymph nodes that are larger than normal, fever, and weight loss. There are many different types of non-Hodgkin lymphoma. For example, non-Hodgkin's lymphoma can be divided into aggressive (fast-growing) and indolent (slow-growing) types. Although non-Hodgkin lymphomas can be derived from B-cells and T-cells, as used herein, the term "non-Hodgkin lymphoma" and "B-cell non-Hodgkin lymphoma" are used interchangeably. B-cell non-Hodgkin lymphomas (NHL) include Burkitt lymphoma, chronic lymphocytic leukemia/small lymphocytic lymphoma (CLL/SLL), diffuse large B-cell lymphoma, follicular lymphoma, immunoblastic large cell lymphoma, precursor B-lymphoblastic lymphoma, and mantle cell lymphoma. Lymphomas that occur after bone marrow or stem cell transplantation are usually B-cell non-Hodgkin lymphomas.

The detection systems of the invention are based, in part, on the ability of a binding agent to bind BCMA or BAFF. Generally, the invention contemplates the use of a binding agent that specifically binds BCMA or BAFF, resulting in the formation of a detectable complex of BCMA or BAFF and binding agent. In one embodiment, the invention utilizes two binding agents, a capture binding agent and a detection binding agent, both of which bind to BCMA, resulting in the formation of a ternary complex comprising capture binding agent, BCMA, and detection binding agent. In another embodiment, the invention utilizes two binding agents, a capture binding agent, and a detection binding agent, both of which bind to BAFF, resulting in the formation of a ternary complex comprising capture binding agent, BAFF, and detection binding agent.

Any of a variety of binding agents may be used, including, for example, polypeptides, sugars, and nucleic acids. In yet another embodiment, the invention further includes the use of an additional binding agent that binds to the detection binding agent. Such an additional binding agent may be useful, e.g., in detecting bound detection binding agent. Accordingly, one example of such an additional binding agent is antibodies specific for a fragment of an antibody, e.g., an Fe fragment, which may be detectably labeled and, therefore used to detect bound detection binding agent, and are particularly useful when the detection binding agent is not itself easily amenable to labeling. In certain embodiments, the binding agent is an antibody specific for bacteria.

The term "binds specifically," in the context of antibody binding, refers to high avidity and/or high affinity binding of an antibody to a specific polypeptide i.e., epitope of a BCMA or BAFF polypeptide. Antibody binding to an epitope on a specific polypeptide (also referred to herein as "an epitope") is preferably stronger than binding of the same antibody to any other epitope, particularly those which may be present in molecules in association with, or in the same sample, as the specific polypeptide of interest, e.g., binds more strongly to a specific BCMA epitope than to a different BCMA epitope or non-BCMA epitope. Antibodies which bind specifically to a polypeptide of interest may be capable of binding other polypeptides at a weak, yet detectable, level (e.g., 10% or less, 5% or less, 1% or less of the binding shown to the polypeptide of interest). Such weak binding, or background binding, is readily discernible from the specific antibody binding to the compound or polypeptide of interest, e.g. by use of appropriate controls. In general, antibodies used in compositions and methods of the invention which bind to a specific BCMA polypeptide with a binding affinity of $10^7$ moles/L or more, preferably $10^8$ moles/L or more are said to bind specifically to the specific BCMA polypeptide. In general, antibodies used in compositions and methods of the invention which bind to a specific BAFF polypeptide with a binding affinity of $10^7$ moles/L or more, preferably $10^8$ moles/L or more are said to bind specifically to the specific BAFF polypeptide. In general, an antibody with a binding affinity of $10^6$ moles/L or less is not useful in that it will not bind an antigen at a detectable level using conventional methodology currently used.

In one embodiment, the affinity of specific binding of a BCMA binding agent to BCMA or the affinity of specific binding of a BAFF binding agent to BAFF is about 2 times greater than background binding, about 5 times greater than background binding, about 10 times greater than background binding, about 20 times greater than background binding, about 50 times greater than background binding, about 100 times greater than background binding, or about 1000 times greater than background binding or more.

In another embodiment, the affinity of specific binding is between about 2 to about 1000 times greater than background binding, between about 2 to 500 times greater than background binding, between about 2 to about 100 times greater than background binding, between about 2 to about 50 times greater than background binding, between about 2 to about 20 times greater than background binding, between about 2 to about 10 times greater than background binding, between about 5 to about 100 times greater than background binding, between about 5 to about 50 times greater than background binding, between about 5 to about 20 times greater than background binding, between about 10 to about 100 times greater than background binding, between about 10 to about 50 times greater than background binding, between about 50 to about 500 times greater than background binding, or any intervening range of affinity.

Accordingly, specific binding occurs between a binding agent and BCMA or BAFF where there is an interaction between the two which produces a bound complex having the characteristics of an antibody/antigen or enzyme/substrate interaction. In a particular embodiment, specific binding is characterized when one member of a pair substantially binds to a particular species and to no other species within the family of compounds to which the corresponding member of the binding member belongs. In another particular embodiment, specific binding is characterized when one member of a pair substantially binds to one or more particular species and to no other species within the family of compounds to which the corresponding member of the binding member belongs. In another particular embodiment, specific binding is characterized when one member of a pair substantially binds to 1, 2, 3, 4, 5, 6, 7, 8, 9, 10, or more particular species and to no other species within the family of compounds to which the corresponding member of the binding member belongs.

Generally speaking, the binding affinity of a binding agent of the invention (A) to BCMA or BAFF (B) can be generally expressed by the chemical equilibrium constant $K_d$ resulting from the following reaction: $[A]+[B]-[AB]$. The chemical equilibrium constant $K_d$ is then given by: $K_d=[A]\times[B]/[AB]$. Whether the binding of a binding agent is specific or not can be judged from the difference between the binding affinity ($K_d$ value) of the binding agent to BCMA or BAFF, versus the binding to another polypeptide.

$K_d$ values and differences in $K_d$ values can be measured using, for example, in vitro or in vivo binding assays and/or assays on other materials such as a polystyrene microtitre plate or a specialized surface in an analytical biosensor. In one embodiment, the difference between the $K_d$ value of a binding agent to BCMA or BAFF, versus the binding to an undesired polypeptide is 2 fold, 3 fold, 4 fold, 5 fold, 6 fold, 7 fold, 8 fold, 9 fold, 10 fold, 20 fold, 50 fold, 100 fold, 1000 fold, or more.

In another embodiment, the $K_d$ value is less than $10^{-4}$ M, less than $10^{-5}$ M, less than $10^{-6}$ M, less than $10^{-7}$ M, less than $10^{-8}$ M, less than $10^{-9}$ M, less than $10^{-10}$ M and could be $10^{-11}$ M, less than $10^{-12}$ M, less than $10^{-13}$ M, less than $10^{-14}$ M, less than $10^{-15}$ M or less.

In another embodiment, the $K_d$ value is between about $10^{-4}$ M and about $10^{-15}$ M, between about $10^{-4}$ M and about $10^{-12}$ M, between about $10^{-4}$ M and about $10^{-10}$ M, between about $10^{-6}$ M and about $10^{-15}$ M, between about $10^{-6}$ M and about $10^{-12}$ M, between about $10^{-6}$ M and about $10^{-10}$ M, between about $10^{-8}$ M and about $10^{-15}$ M, between about $10^{-8}$ M and about $10^{-12}$ M, between about $10^{-8}$ M and about $10^{-10}$ M, between about $10^{-7}$ M and about $10^{-10}$ M, or any intervening range of affinity The term "antibody" herein is used in the broadest sense and specifically covers monoclonal antibodies, polyclonal antibodies, multispecific antibodies (e.g., bispecific antibodies) formed from at least two intact antibodies, and antibody fragments so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that can be present in minor amounts. In one embodiment, the monoclonal antibody is an anti-BCMA monoclonal antibody.

In one embodiment, the monoclonal antibody is an anti-BAFF monoclonal antibody.

Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256: 495 (1975), or may be made by recombinant DNA methods (see, e.g., U.S. Pat. No. 4,816,567). The "monoclonal antibodies" may also be isolated from phage antibody libraries using the techniques described in Clackson et al., Nature, 352: 624-628 (1991) and Marks et al., J. Mol. Biol., 222: 581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain (s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81: 6851-6855 (1984)). Methods of making chimeric antibodies are known in the art.

"Humanized" forms of non-human (e.g., murine) antibodies are chimeric immunoglobulins, immunoglobulin chains or fragments thereof (such as Fv, Fab, Fab', F (ab') 2 or other antigen-binding subsequences of antibodies) which contain minimal sequence derived from non-human immunoglobulin.

For the most part, humanized antibodies are human immunoglobulins (recipient antibody) in which residues from a complementarity-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence although the FR regions may include one or more amino acid substitutions that improve binding affinity. The number of these amino acid substitutions in the FR is typically no more than 6 in the H chain, and no more than 3 in the L chain.

The humanized antibody optimally also will comprise at least a portion of an immunoglobulin constant region (Fc), typically that of a human immunoglobulin. For further details, see Jones et al., Nature, 321: 522-525 (1986); Reichmann et al., Nature, 332: 323-329 (1988); and Presta, Curr. Op. Struct. Biol., 2: 593-596 (1992). The humanized antibody includes a PRIMATIZED antibody wherein the antigen-binding region of the antibody is derived from an antibody produced by, e.g., immunizing macaque monkeys with the antigen of interest. Methods of making humanized antibodies are known in the art.

Human antibodies can also be produced using various techniques known in the art, including phage-display libraries. Hoogenboom and Winter, J. Mol. Biol., 227: 381 (1991); Marks et al., J. Mol. Biol., 222: 581 (1991). The techniques of Cole et al. and Boerner et al. are also available for the preparation of human monoclonal antibodies. Cole et al., Monoclonal Antibodies and Cancer Therapy, Alan R. Liss, p. 77 (1985); Boerner et al., J. Immunol., 147(1): 86-95 (1991).

"Functional fragments" of the binding antibodies of the invention are those fragments that retain binding to antigen with substantially the same affinity as the intact full chain molecule from which they are derived.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The terms "detectably labeled antibody" refers to an antibody (or antibody fragment which retains binding specificity for a BCMA or BAFF polypeptide or epitope), having an attached detectable label. The detectable label is normally attached by chemical conjugation, but where the label is a polypeptide, it could alternatively be attached by genetic engineering techniques. Methods for production of detectably labeled proteins are well known in the art. Detectable labels may be selected from a variety of such labels known in the art, including, but not limited to, haptens, radioisotopes, fluorophores, paramagnetic labels, enzymes (e.g., horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/diaminobenzidine, avidin/streptavidin, luciferase/luciferin)), methods for labeling antibodies, and methods for using labeled antibodies are well known in the art (see, for example, Harlow and Lane, eds. (*Antibodies: A Laboratory Manual* (1988) Cold Spring Harbor Laboratory Press, Cold Spring Harbor, N.Y.)).

In one technique, an immunogen comprising the polypeptide is initially injected into any of a wide variety of mammals (e.g., mice, rats, rabbits, sheep or goats). Polyclonal antibodies specific for the polypeptide may then be purified from such antisera by, for example, affinity chromatography using the polypeptide coupled to a suitable solid support. In one embodiment, the antibody is an anti-BCMA polyclonal antibody. In one embodiment, the antibody is an anti-BAFF polyclonal antibody.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived there from and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, urine, cerebral spinal fluid, biological fluid, and tissue samples. The sample may be pretreated as necessary by dilution in an appropriate buffer solution or concentrated, if desired. Any of a number of standard aqueous buffer solutions, employing one of a variety of buffers, such as phosphate, Tris, or the like, preferably at physiological pH can be used. Biological samples can be derived from patients using well known techniques such as venipuncture, lumbar puncture, fluid sample such as saliva or urine, or tissue biopsy and the like.

As used herein, the terms "correlated with" or "associated with" refer to the levels of BCMA or BAFF in a biological sample of a subject that has a statistically significant correlation with a physiologic state, e.g., disease status or extent of the disease, response to treatment, and survival. The strength of the correlation between BCMA or BAFF levels and the presence or absence of a particular physiologic state may be determined by a statistical test of significance. Methods for determining the strength of a correlation between the expression level of a differentially-expressed gene and a particular physiologic state by assigning a statistical score to the correlation are reviewed in Holloway et al. (2002) *Nature Genetics* Suppl. 32:481-89, Churchill (2002) *Nature Genetics* Suppl. 32:490-95, Quackenbush (2002) *Nature Genetics* Suppl. 32: 496-501; Slonim (2002) *Nature Genetics* Suppl. 32:502-08; and Chuaqui et al. (2002) *Nature Genetics* Suppl. 32:509-514; each of which is herein incorporated by reference in its entirety.

A "conjugate" refers to any molecule, e.g., antibody bound or joined covalently or non-covalently to another molecule, e.g., a hapten, small molecule, or label. including fusion proteins and as well as molecules that contain both amino acid or protein portions and non-protein portions. Conjugates may be synthesized by a variety of techniques known in the art including, for example, solid phase synthesis, solution phase synthesis, organic chemical synthetic techniques or a combination of these techniques. The choice of synthesis will depend upon the particular molecule to be generated.

The terms "individual," "subject," and "patient," used interchangeably herein, refer to a mammal, including, but not limited to, murines, simians, humans, mammalian farm animals, mammalian sport animals, and mammalian pets. The term "mammal" refers to any animal classified as a mammal, including humans, domestic and farm animals, and zoo, sports, or pet animals, such as dogs, horses, cats, cows, etc. Preferably, the mammal herein is human.

C. Methods of Diagnosis, Prognosis and Monitoring of Multiple Myeloma, Chronic Lymphocytic Leukemia, and B-Cell Non-Hodgkin Lymphoma The present inventors have discovered that B-cell maturation antigen (BCMA) levels are increased in the serum of MM, CLL, and NHL patients compared to normal healthy subjects not these cancers. Accordingly, particular embodiments of the invention provide methods and compositions for the diagnosis of multiple myeloma, prognosis of survival in patients diagnosed with MM, CLL, or NHL as well as monitoring the response of the disease to treatment, based upon the level of BCMA observed in a biological sample obtained from a patient, including, e.g., a patient's bloodstream, serum, bone marrow, or tissue. A variety of methods of determining BCMA levels are known and available in the art. In certain embodiments, these involve the use of a BCMA binding agent, such as a BCMA specific antibody. As discussed elsewhere herein, there are a variety of assay formats known to those of ordinary skill in the art and suitable for using a binding agent to detect polypeptide markers in a sample. E.g., ELISA assays, lateral flow assays, etc.; see also, Harlow and Lane, *Antibodies: A Laboratory Manual*, Cold Spring Harbor Laboratory, 1988.

In general, MM, CLL, or NHL is diagnosed by the presence of at least 2-fold, at least 5-fold, at least 10-fold, at least 20-fold, at least 50-fold, at least 100-fold, at least 1000-fold, or higher levels of BCMA as compared to those in a normal control subject. In general, methods of diagnosing MM, CLL, or NHL comprise: (a) detecting an amount of BCMA in a biological sample, e.g., serum, obtained from a subject; and (b) comparing the amount detected in step (a) to a predetermined cut-off value or to an amount detected in a control biological sample, wherein an increased amount of BCMA in the biological sample of (a) as compared to the predetermined cut-off value or amount in the control biological sample of (b) indicates the presence of MM, CLL, or NHL, and diagnosing the subject with MM, CLL, or NHL.

In one embodiment, a method of prognosis for the survival of a subject having MM, CLL, or NHL is provided. In general, a subject diagnosed with and/or treated for MM, CLL, or NHL and having an amount of serum BCMA detected that is more than a median value of serum BCMA detected in a population of subjects being treated for MM, CLL, or NHL has a poorer chance of survival compared to the subjects in the population having less than or equal to the median serum BCMA levels. In particular embodiments, a subject having serum BCMA levels greater than the median value in a population being treated for MM, CLL, or NHL has a reduced chance of survival of about 10%, about 20%, about 30%, about 40%, about 50%, about 60%, about 70% or more.

In general, a method of prognosis for the survival of a subject having MM, CLL, or NHL comprises: (a) detecting an amount of BCMA in a biological sample, e.g., serum, obtained from a subject; and (b) comparing the amount detected in step (a) to a the median value of serum BCMA levels in a population of subjects being treated for MM, CLL, or NHL, wherein an increased amount of BCMA in the biological sample of (a) as compared to the median value or corresponding amount in the treated population of (b) indicates a reduced chance of survival for the subject having MM, CLL, or NHL.

Being able to predict the reduced chance of survival is advantageous because it allows the clinician to change the therapeutic course in the hopes of increasing the chance of survival of the subject.

In a certain embodiment, a method of monitoring the progression or response to treatment of MM, CLL, or NHL is provided. A method of monitoring the progression or response to treatment of MM, CLL, or NHL comprises: (a) detecting an amount of BCMA in a biological sample, e.g., serum, obtained from a subject diagnosed with MM, CLL, or NHL at a first time point; (b) detecting an amount of BCMA in a biological sample obtained from the subject at a second time point or following treatment; and (c) comparing the amount detected in step (a) to the amount detected in step (b), wherein an increased amount of BCMA in the biological sample of (b) as compared to the amount in the biological sample of (a) indicates that said MM, CLL, or NHL is progressing, and wherein a decreased amount of BCMA in the biological sample of (b) as compared to the amount in the biological sample of (a) indicates that said MM, CLL, or NHL is entering remission or responding to treatment.

In various embodiments of methods of detecting BCMA, a biological sample is selected from the group consisting of: serum, bone marrow, and tissue. In particular embodiments, mRNA levels are determined, while in other preferred embodiments, polypeptide levels are determined. In one embodiment, detection is performed using one or more primers specific for BCMA. In another preferred embodiment, detection is performed using an antibody specific for BCMA.

In one embodiment, the presence or absence of MM, CLL, or NHL in a patient may be determined by (a) contacting a biological sample obtained from a patient with a BCMA binding agent; (b) detecting in the sample a level of BCMA polypeptide that binds to the binding agent; and (c) comparing the level of BCMA polypeptide with a predetermined cut-off value or with the value obtained from a normal control subject. In certain embodiments, the cut-off value for the detection of a MM, CLL, or NHL is the average mean signal obtained when the immobilized antibody is incubated with samples from patients without MM, CLL, or NHL.

In particular embodiments, a sample generating a signal that is three standard deviations above the predetermined cut-off value is considered positive for MM, CLL, or NHL. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106-7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for MM, CLL, or NHL.

In one embodiment, the assay involves the use of a BCMA binding agent immobilized on a solid support to bind to and remove the BCMA polypeptide from the remainder of the sample. The bound BCMA polypeptide may then be detected using a detection reagent that contains a reporter group and specifically binds to the binding agent/polypeptide complex. Such detection reagents may comprise, for example, a binding agent that specifically binds to the BCMA polypeptide or an antibody or other agent that specifically binds to the binding agent, such as an antiimmunoglobulin, protein G5 protein A or a lectin.

In a related embodiment, the assay is performed in a lateral flow or strip test format, as discussed elsewhere herein, wherein the BCMA binding agent, e.g., antibody, is immobilized on a membrane, such as nitrocellulose. In the lateral flow test, BCMA polypeptides within the sample bind to the immobilized binding agent as the sample passes through the membrane. A second, labeled binding agent then binds to the BCMA binding agent-polypeptide complex as a solution containing the second binding agent flows through the membrane. The detection of bound second binding agent may then be performed as described above. In the strip test format, one end of the membrane to which BCMA binding agent is bound is immersed in a solution containing the sample. The sample migrates along the membrane through a region containing second binding agent and to the area of immobilized binding agent. Concentration of second binding agent at the area of immobilized antibody indicates the presence of MM, CLL, or NHL.

The invention provides similar methods for staging or monitoring the progression of MM, CLL, or NHL, as well as determining response to treatment. Since serum BCMA levels correlate with severity or extent of the disease, levels associated with particular stages are determined and compared to those observed in a subject's serum to determine the stage of the subject's disease. Similarly, disease progression and response to treatment or therapy is monitored by comparing BCMA levels in a subject's serum (or other biological sample) at different time points during the course of the disease or before and after a treatment regimen. In particular embodiments, BCMA serum levels are elevated in MM, CLL, or NHL patients, and the levels of BCMA correlate with disease stage, i.e., BCMA levels are higher in progressive MM, CLL, or NHL and become lower in response to treatment or entering remission. Thus, the present invention provides a rapid and reliable method of detecting, diagnosing, prognosis, staging, and monitoring progression or response to treatment of MM, CLL, or NHL disease, using a serum sample obtained from the subject's bloodstream. In particular embodiments, the method is practiced by ELISA assay, lateral flow assay, or strip test assay using an antibody specific for BCMA.

The invention further provides systems and kits for detecting, diagnosing, prognosing, staging, or monitoring multiple myeloma, which comprise reagents suitable or determining BCMA levels in a biological, e.g., serum, sample obtained from a subject. In one embodiment, the kit includes reagents for performing ELISA, lateral flow, or strip test assays such as an antibody specific for BCMA. Detection systems and kits of the invention are described in further detail below.

In addition, the present inventors have discovered that BAFF levels are decreased in the serum of MM, CLL, and NHL patients compared to normal healthy subjects that do not have these cancers. Accordingly, particular embodiments of the invention provide methods and compositions for the diagnosis of multiple myeloma, prognosis of survival in patients diagnosed with MM, CLL, or NHL as well as monitoring the response of the disease to treatment, based upon the level of BAFF observed in a biological sample obtained from a patient, including, e.g., a patient's bloodstream, serum, bone marrow, or tissue. A variety of methods of determining BAFF levels are known and available in the art.

In general, MM, CLL, or NHL is diagnosed by the presence of at least 2-fold, at least 5-fold, at least 10-fold, at least 20-fold, at least 50-fold, at least 100-fold, at least 1000-fold, or lower levels of BAFF as compared to those in a normal control subject. In general, methods of diagnosing MM, CLL, or NHL comprise: (a) detecting an amount of BAFF in a biological sample, e.g., serum, obtained from a subject; and (b) comparing the amount detected in step (a) to a predetermined cut-off value or to an amount detected in a control biological sample, wherein a decreased amount of BAFF in the biological sample of (a) as compared to the predetermined cut-off value or amount in the control biological sample of (b) indicates the presence of MM, CLL, or NHL, and diagnosing the subject with MM, CLL, or NHL.

In one embodiment, a method of prognosis for the survival of a subject having MM, CLL, or NHL is provided. In general, a subject diagnosed with and/or treated for MM, CLL, or NHL and having an amount of serum BAFF detected that is less than a median value of serum BAFF detected in a population of subjects being treated for MM, CLL, or NHL has a poorer chance of survival compared to the subjects in the population having more than or equal to the median serum BAFF levels. In particular embodiments, a subject having serum BAFF levels lower than the median value in a population being treated for MM, CLL, or NHL has a reduced chance of survival of about 10%, about 20%, about 30%, about 40%, about 50%, about 60%, about 70% or more.

In general, a method of prognosis for the survival of a subject having MM, CLL, or NHL comprises: (a) detecting an amount of BAFF in a biological sample, e.g., serum, obtained from a subject; and (b) comparing the amount detected in step (a) to a the median value of serum BAFF levels in a population of subjects being treated for MM, CLL, or NHL, wherein a decreased amount of BAFF in the biological sample of (a) as compared to the median value or corresponding amount in the treated population of (b) indicates a reduced chance of survival for the subject having MM, CLL, or NHL.

In a certain embodiment, a method of monitoring the progression or response to treatment of MM, CLL, or NHL is provided. A method of monitoring the progression or response to treatment of MM, CLL, or NHL comprises: (a) detecting an amount of BAFF in a biological sample, e.g., serum, obtained from a subject diagnosed with MM, CLL, or NHL at a first time point; (b) detecting an amount of BAFF in a biological sample obtained from the subject at a second time point or following treatment; and (c) comparing the amount detected in step (a) to the amount detected in step (b), wherein a decreased amount of BCMA in the biological sample of (b) as compared to the amount in the biological sample of (a) indicates that said MM, CLL, or NHL is worsening, and wherein an increased amount of BCMA in the biological sample of (b) as compared to the amount in the biological sample of (a) indicates that said MM, CLL, or NHL is entering remission or responding to treatment.

In various embodiments of methods of detecting BAFF, a biological sample is selected from the group consisting of: serum, bone marrow and tissue. In particular embodiments, mRNA levels are determined, while in other preferred embodiments, polypeptide levels are determined. In one embodiment, detection is performed using one or more primers specific for BAFF. In another preferred embodiment, detection is performed using an antibody specific for BAFF.

In one embodiment, the presence or absence of MM, CLL, or NHL in a patient may be determined by (a) contacting a biological sample obtained from a patient with a BAFF binding agent; (b) detecting in the sample a level of BAFF polypeptide that binds to the binding agent; and (c) comparing the level of BAFF polypeptide with a predetermined cut-off value or with the value obtained from a normal control subject. In certain embodiments, the cut-off value for the detection of a MM, CLL, or NHL is the average mean signal obtained when the immobilized antibody is incubated with samples from patients without MM, CLL, or NHL.

In particular embodiments, a sample generating a signal that is three standard deviations below the predetermined cut-off value is considered positive for MM, CLL, or NHL.

In one embodiment, the assay involves the use of a BAFF binding agent immobilized on a solid support to bind to and remove the BAFF polypeptide from the remainder of the sample. The bound BAFF polypeptide may then be detected using a detection reagent that contains a reporter group and specifically binds to the binding agent/polypeptide complex. Such detection reagents may comprise, for example, a binding agent that specifically binds to the BAFF polypeptide or an antibody or other agent that specifically binds to the binding agent, such as an antiimmunoglobulin, protein G5 protein A or a lectin.

In a related embodiment, the assay is performed in a lateral flow or strip test format, as discussed elsewhere herein, wherein the BAFF binding agent, e.g., antibody, is immobilized on a membrane, such as nitrocellulose. In the lateral flow test, BAFF polypeptides within the sample bind to the immobilized binding agent as the sample passes through the membrane. A second, labeled binding agent then binds to the BCMA binding agent-polypeptide complex as a solution containing the second binding agent flows through the membrane. The detection of bound second binding agent may then be performed as described above. In the strip test format, one end of the membrane to which BAFF binding agent is bound is immersed in a solution containing the sample. The sample migrates along the membrane through a region containing second binding agent and to the area of immobilized binding agent. Concentration of second binding agent at the area of immobilized antibody indicates the presence of BAFF.

The invention provides similar methods for staging or monitoring the progression of MM, CLL, or NHL, as well as determining response to treatment. Since serum BAFF levels correlate with severity or extent of the disease, levels associated with particular stages are determined and compared to those observed in a subject's serum to determine the stage of the subject's disease. Similarly, disease progression and response to treatment or therapy is monitored by comparing BAFF levels in a subject's serum (or other biological sample) at different time points during the course of the disease or before and after a treatment regimen. In particular embodiments, serum BAFF levels are decreased in MM, CLL, or NHL patients, and the levels of BAFF correlate with disease stage, i.e., levels are lower in progressive MM, CLL, or NHL and increase in response to treatment or entering remission. Thus, the present invention provides a rapid and reliable method of detecting, diagnosing, prognosis, staging, and monitoring progression or response to treatment of MM, CLL, or NHL disease, using a serum sample obtained from the subject's bloodstream. In particular embodiments, the method is practiced by ELISA assay, lateral flow assay, or strip test assay using an antibody specific for BAFF.

The invention further provides systems and kits for detecting, diagnosing, prognosing, staging, or monitoring multiple myeloma, which comprise reagents suitable or determining BAFF levels in a biological, e.g., serum, sample obtained from a subject. In one embodiment, the kit includes reagents for performing ELISA, lateral flow, or strip test assays such as an antibody specific for BAFF. Detection systems and kits of the invention are described in further detail below.

D. Detection Systems and Kits

In various embodiments, the present invention provides detection systems and kits for MM, CLL, or NHL. A detection system or kit of the present invention may be used for diagnosis, prognosis, or monitoring of MM, CLL, or NHL patients in a biological sample, e.g., serum, of a subject. The diagnostic kit could include the method for the detection of antigen-antibody reaction in addition to the material. The detection method is preferably selected from the group consisting of flow cytometry, immunohistochemistry, and enzyme-linked immunosorbent assay (ELISA), radioimmunoassay (RIA), enzyme immunoassay (EIA), fluorescence immunoassay (FIA), luminescence immunoassay (LIA), lateral flow assays and strip assay. The reactivity of the antigen recognition material could be confirmed using device detecting an enzyme reaction, fluorescence, luminescence, or radiation. In one embodiment, the diagnosis, prognosis, or monitoring of MM, CLL, or NHL can be made with a flow cytometry kit, immunohistochemistry kit, ELISA kit or lateral flow or strip kit including the anti-BCMA antibody or an antigen binding fragment thereof.

In one embodiment, the diagnosis, prognosis, or monitoring of MM, CLL, or NHL can be made with a flow cytometry kit, immunohistochemistry kit, ELISA kit or lateral flow or strip kit including the anti-BAFF antibody or an antigen binding fragment thereof.

In one embodiment, a kit or system may comprise one or more or all of the following components: 1) one or more standards comprised of one or more of the biomarker(s) of the invention, such as BCMA or BAFF; 2) a binding agent, such as an antibody or a plurality of antibodies, that are specific for the biomarker(s) that are to be assayed for using the kit; 3) written instructions; 4) diluents for samples and the standards; 5) a wash buffer; 6) color reagents; 7) stop solution; and 8) a carrier, such as an antibody carrier, for example, a lateral flow device, or a microplate with bound antibody, or polystyrene beads.

In one embodiment, the detection system or kit used to diagnose, prognose, or monitor MM, CLL, or NHL is a quantitative ELISA (enzyme-linked immunosorbent assay) that determines the concentration or concentrations of the biomarker or biomarker(s) in accordance with methods embodied by the invention. The principle of the assay is to use the quantitative sandwich enzyme immunoassay technique wherein a monoclonal or polyclonal antibody selective for a biomarker is pre-coated onto a carrier such as a microplate into its wells. The standards and sample are then pipetted into the wells and any of the biomarker that is present is bound to this immobilized antibody. Next, the wells are washed with washing buffer, and an enzyme-linked monoclonal or polyclonal antibody that is specific for the biomarker is added to the wells. Washing is again performed, then a substrate solution is added to the wells. Color subsequently develops in proportion to the amount of polypeptide of the invention that is bound in the first step. The color development is stopped using a stop solution, and the intensity of the color is measured by a microplate reader.

In other embodiments, the diagnosis, prognosis, or monitoring of MM, CLL, or NHL may be carried out using, for example, a lateral flow assay. Such lateral flow assays have the potential to be a cost-effective, fast, simple, and sensitive method, for instance for on-site screening assays. The lateral flow assay comprises a carrier that allows a lateral flow to occur wherein either the sample or the detection reagent is displaced form one location on the carrier to another. There are many formats of lateral flow assays suitable for use in a method embodied by the invention, and the skilled person will readily know how to select and optimize a particular format. An example of a lateral flow test strip of the invention comprises, for example, the following components: sample pad; an absorbent pad onto which the test sample is applied; a conjugate or reagent pad that contains antibodies specific to the target analyte and conjugated to colored particles (usually colloidal gold particles, or latex microspheres); a reaction membrane, typically a hydrophobic nitrocellulose or cellulose acetate membrane onto which anti-target analyte antibodies are immobilized in a line across the membrane as a capture zone or test line (a control zone may also be present, containing antibodies specific for the conjugate antibodies); and a wick or waste reservoir, a further absorbent pad designed to draw the sample across the reaction membrane by capillary action and collect it.

There are a number of variations on lateral flow technology. The capture zone on the membrane may contain immobilized antigens or enzymes depending on the target analyte rather than antibodies. It is also possible to apply multiple capture zones to create a multiplex test. For example, in particular embodiments, test strips able to detect BCMA or BAFF and separately in the same sample additional biomarkers of multiple myeloma, e.g., $\beta 2M$, IL-6, C-reactive protein, and serum monoclonal protein are contemplated. Lateral flow immunoassays are simple to use by untrained operators and generally produce a result within 15 minutes. They are very stable and robust, have a long shelf life and do not usually require refrigeration. They are also relatively inexpensive to produce. These features make them ideal for use at the point-of-care and for testing samples in the field, as well as in the laboratory.

While most lateral flow immunoassays are only capable of providing a qualitative result, it is possible to obtain some degree of quantification by measuring the amount of conjugate bound to the capture zone. This can be done using a dedicated reader to measure the intensity of the colored test line. For example, the Neogen Corporation has developed the Accuscan™ lateral flow reader for use with its range of Reveal® assay kits and Charm Sciences also supplies a reader for its Rosa® range of test strips. More sophisticated techniques, such as fluorescent dye labeled conjugates, have also been developed to improve the quantitative potential of lateral flow assays.

A detection system in kit form can include, for example, in an amount sufficient for at least one assay and an antibody composition or monoclonal antibody composition that binds a serological biomarker for MM, CLL, or NHL, as a packaged reagent. Instructions for use of the packaged reagent are also typically included.

A detection system in kit form can also include, for example, a means for combining the test sample with a buffering system (Reagent 1) containing viscosity controllers and stabilizers into a reaction vessel and mixing the solution. A detection system in kit form can also include a means for reading the a parameter of the reaction vessel with sample and buffer, and further means for combining the test sample and buffer mixture with a fluorescence-labeled ligand (Reagent 2) to said biological substance in the reaction vessel, mixing the solution to produce an assay solution. Furthermore, Reagent 2 may be delivered to the reaction vessel without further dilution volume of the assay solution.

As used herein, the term "package" refers to a solid matrix or material such as glass, plastic, paper, foil and the like capable of holding within fixed limits an antibody composition or monoclonal antibody composition. Thus, for example, a package can be a glass vial used to contain milligram quantities of a contemplated polypeptide or it can be a microtiter plate well to which microgram quantities of a contemplated polypeptide or antibody have been operatively affixed.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In particular embodiments, a detection system of the present invention further includes a label or indicating means capable of signaling the formation of a complex containing a polypeptide or antibody molecule of the present invention.

"Complex" as used herein refers to the product of a specific binding reaction such as an antibody-antigen or receptor-ligand reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents such labels are themselves well-known in clinical diagnostic chemistry and constitute a part of this invention only insofar as they are utilized with otherwise novel proteins methods and/or systems.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyante (FITC), 5-dimethylamine-1-naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", in *Antibody As a Tool*, Marchalonis, et al., eds., John Wiley & Sons, Ltd., pp. 189-231 (1982), which is incorporated herein by reference.

In certain embodiments, the indicating group is an enzyme, such as horseradish peroxidase (HRP), glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-azino-di-(3-ethyl-benzthiazoline-G-sulfonic acid) (ABTS).

Radioactive elements are also useful labeling agents and are used illustratively herein. An exemplary radiolabeling agent is a radioactive element that produces gamma ray emissions. Elements which themselves emit gamma rays, such as $^{124}$I, $^{125}$I, $^{128}$I, $^{132}$I and $^{51}$Cr represent one class of gamma ray emission-producing radioactive element indicating groups. Particularly preferred is $^{125}$I. Another group of useful labeling means are those elements such as $^{11}$C, $^{18}$F, $^{15}$O and $^{13}$N which themselves emit positrons. The positrons so emitted produce gamma rays upon encounters with electrons present in the animal's body. Also useful is a beta emitter, such $^{111}$indium or $^{3}$H.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., *Meth. Enzymol.*, 73:3-46 (1981). The techniques of protein conjugation or coupling through activated functional groups are particularly applicable. See, for example, Aurameas, et al., *Scand. J. Immunol.*, Vol. 8 Suppl. 7:7-23 (1978), Rodwell et al., *Biotech.*, 3:889-894 (1984), and U.S. Pat. No. 4,493,795, which are all incorporated herein by reference.

The detection systems or kits of the present invention can be used in an "ELISA" format to detect, for example, the presence or quantity of BCMA or BAFF in a body fluid sample such as the bloodstream, serum, bone marrow, or tissue, etc. "ELISA" refers to an enzyme-linked immunosorbent assay that employs an antibody or antigen bound to a solid phase and an enzyme-antigen or enzyme-antibody conjugate to detect and quantify the amount of an antigen or antibody present in a sample. Thus, for example, a polypeptide, antibody molecule composition or monoclonal antibody molecule composition of the present invention can be affixed to a solid matrix to form a solid support that comprises a package in the subject diagnostic systems. The reagent is typically affixed to the solid matrix by adsorption from an aqueous medium although other modes of affixation, well known to those skilled in the art, can be used.

Useful solid matrices are also well known in the art. Such materials are water insoluble and include cross-linked dextran; agarose; beads of polystyrene beads about 1 micron to about 5 millimeters in diameter; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any detection system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this detection assay system.

The packaging materials discussed herein in relation to detection systems are those customarily utilized in diagnostic systems. Such materials include glass and plastic (e.g., polyethylene, polypropylene and polycarbonate) bottles, vials, plastic and plastic-foil laminated envelopes and the like. In one embodiment, a detection system of the present invention is useful for assaying for the presence of, for example, BCMA or BAFF. Such a system comprises, in kit form, a package containing an antibody to, for example, BCMA or BAFF.

All publications, patent applications, and issued patents cited in this specification are herein incorporated by reference as if each individual publication, patent application, or issued patent were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

BMMCs from MM Patients Showed BCMA Expression and Culture Medium from these Cells Showed High BCMA Concentrations The membrane-bound B-cell maturation antigen (BCMA) expression on bone marrow mononuclear cells (BMMCs) from multiple myeloma (MM) patients and healthy subjects ($1 \times 10^4$ cells) was measured using flow cytometric analysis. BCMA protein was detected on a very small proportion of BMMCs from healthy subjects whereas most BMMCs from MM patients showed strong BCMA staining (FIG. 1). BCMA expression was also strong in peripheral blood mononuclear cells (PBMCs) from a patient with plasma cell leukemia (FIG. 1). The presence of BCMA in CD138- expressing and light chain-restricted BMMCs from MM patients (data not shown) was also confirmed.

Figure 2A:
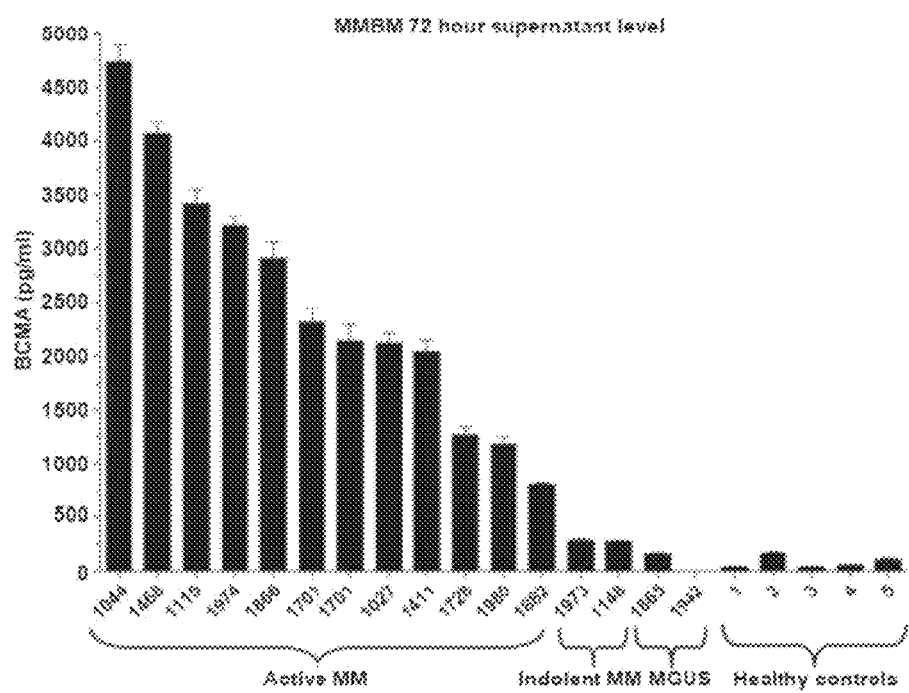
FIGS. 2A-2B show that BCMA is found in supernatants from cultured BMMCs from MM patients.

BMMCs ($1.6 \times 10^6$ cells/well) from MM patients with active disease (n=12 samples) or indolent disease (n=2), two MGUS individuals, and five healthy subjects were cultured for 72 h to determine if MM cells from BM are capable of releasing BCMA into the culture medium. Supernatants from MM patients showed high BCMA concentrations, whereas those from healthy subjects showed negligible amounts (FIG. 2A). BCMA supernatant levels were markedly higher in MM patients with active disease than among those with indolent MM or MGUS (FIG. 2A). BCMA was not detectable in the supernatants from PBMCs from MM patients, except for a very high concentration (1589 pg/ml) in a patient with plasma cell leukemia who lost the presence of measurable monoclonal Ig (data not shown). These findings demonstrate that high amounts of BCMA are released from MM-containing PB or BM MCs.

Example 2

Supernatant BCMA Levels Correlated with the Percentage of MM Plasma Cells

Figure 2B:
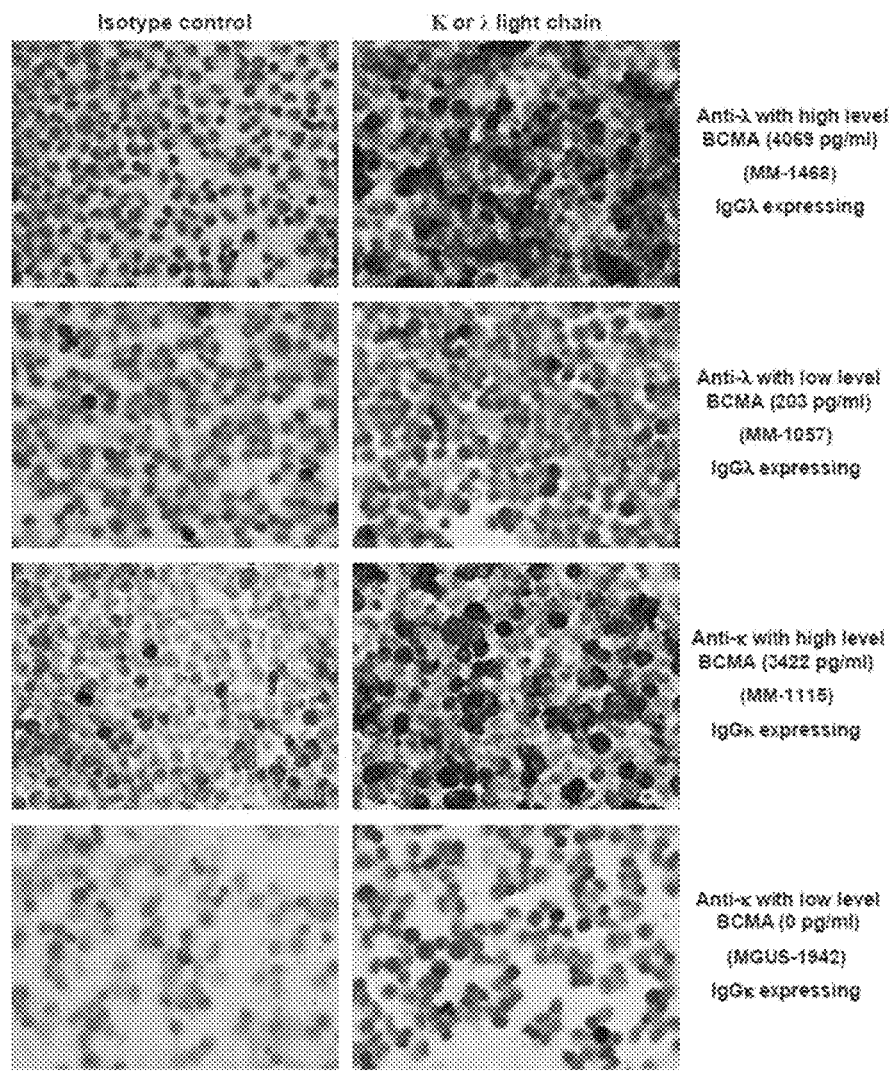

The concentrations of BCMA in the culture medium correlated with the percentage of MM plasma cells in the BMMCs. H&E and λ and κ light chain staining was performed to identify malignant plasma cells. Total numbers of nucleated cells and plasma cells were counted and the proportions of malignant cells were calculated. Patients with a high percentage of malignant cells (>70% of MM tumor cells) as determined by the proportion of cells showing light chain staining, demonstrated high concentrations of BCMA in their culture medium whereas those with few light chain staining cells had low BCMA levels in their culture medium (FIG. 2B).

Example 3

Serum BCMA Levels were Elevated in MM Patients

BCMA levels in sera from patients with newly diagnosed MM (n=50), MGUS individuals (n=23) and healthy control subjects (n=40) that were age- and gender-matched were measured. The MM patients included those with IgGκ (n=24), IgGλ (n=9), IgAκ (n=6), IgAλ (n=3), IgMκ (n=1), κ light chain only (n=4), and λ light chain only (n=3) disease. The International Staging System (Greipp et al., 2005) was used; 30, 12 and seven patients were stages 1, 2, and 3 respectively, and one was unknown. The serum levels of BCMA in MM patients were elevated when compared to healthy controls (P<0.0001) and MGUS individuals (P=0.0157; FIG. 3A). In particular, the median serum BCMA concentrations in MM, MGUS and controls were 13.87 ng/mL, 5.30 ng/mL, and 2.57 ng/mL, respectively.

Indolent MM patients (n=16) had lower levels (median 11.60 ng/mL) than among those with active MM (n=34, median 17.79 ng/mL). In addition, one MGUS patient who eventually progressed to MM had the highest serum BCMA level (12.62 ng/mL) of MGUS patients, which had more than doubled to 25.68 ng/mL at the time she developed MM.

BCMA levels did not correlate with serum creatinine levels (data not shown). Cross-reactivity of the ELISA with a high concentration of human IgG (1000 ng/mL) was negligible, with a BCMA readout of only 0.015 ng/mL (data not shown).

Example 4

Serum BCMA Levels in MM Patients Correlated with Supernatant from Cultured MM BMMCs, Disease Status and Overall Survival

Figure 4:
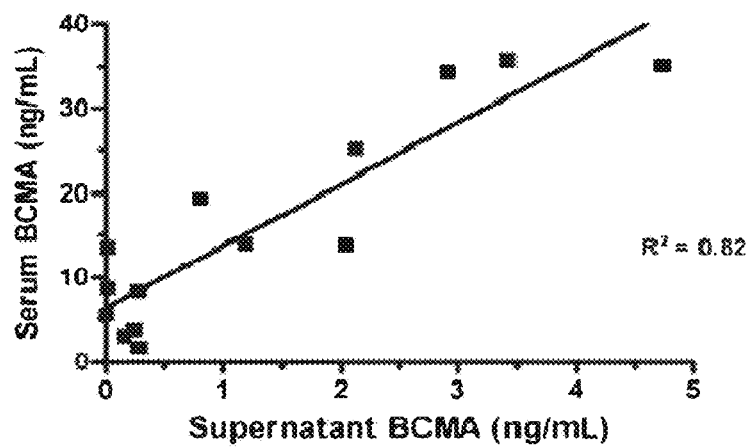
FIG. 4 shows a correlation of serum BCMA levels with supernatant BCMA concentrations. Serum from a Corvac™ serum separator tube (Becton Dickinson, Franklin Lakes, NJ) was isolated by centrifugation and stored at −80° C. BM aspirates were collected in heparinized tubes and MCs were isolated using density-gradient centrifugation with Histopaque-1077 (Sigma-Aldrich, St. Louis, MO). Cells were cultured in RPMI1640 (Omega Scientific, Tarzana, CA) supplemented with 10% FBS, nonessential amino acids, 2 mM glutamine, 1 mM sodium pyruvate, 25 mM HEPES, 200 units/mL penicillin, and streptomycin at 37° C. and 5% $CO_2$. Supernatants were collected after 72 hours of culturing MCs from BM aspirates from MM patients.
Figure 5A:
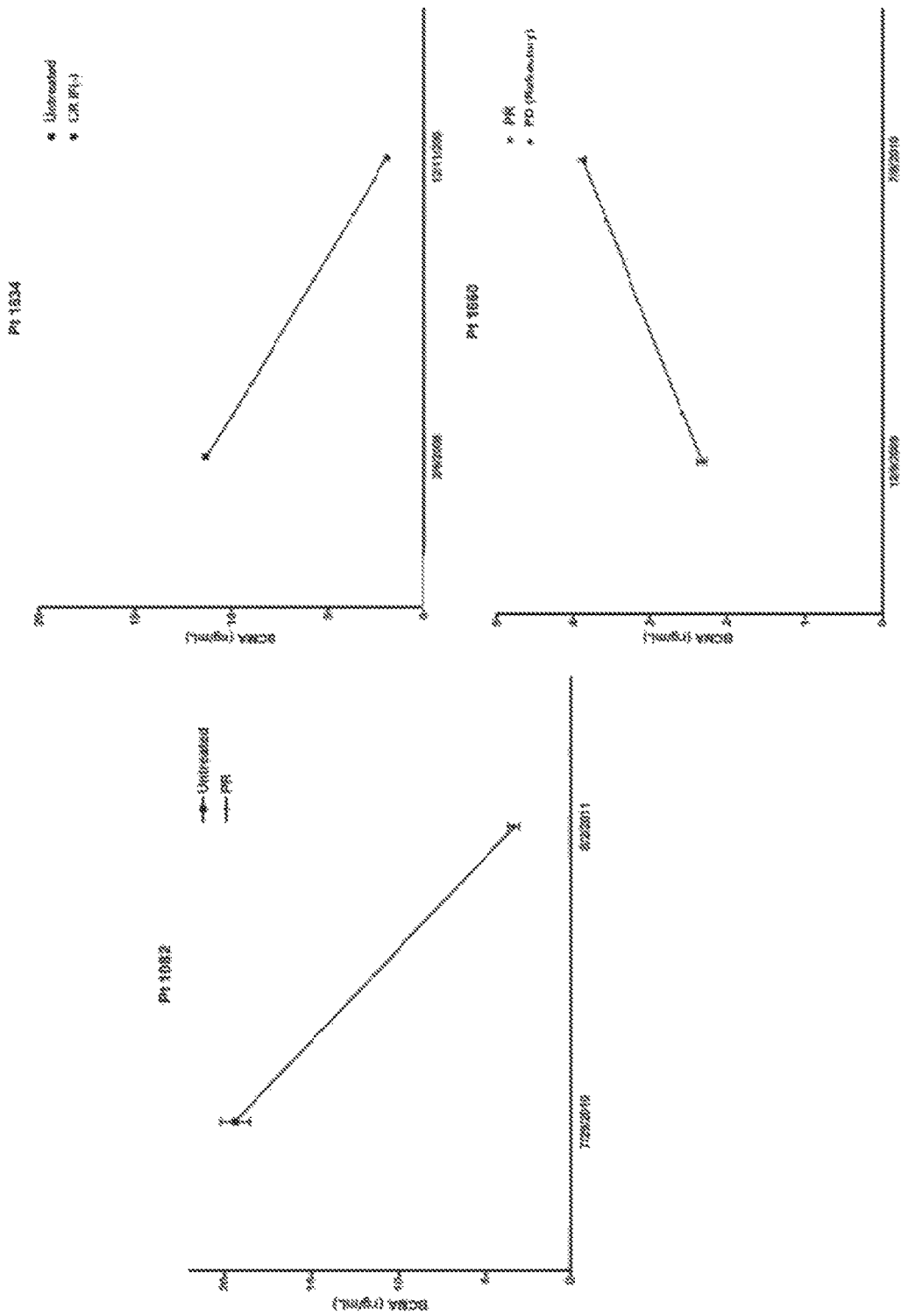
FIGS. 5A-5J show that changes in serum BCMA levels were found to correlate with changes in individual patient's clinical status in response to anti-MM treatment. During the course of an individual MM patient's treatment, serum BCMA levels were measured with an ELISA and graphed. In one patient (2015.
Figure 5B:
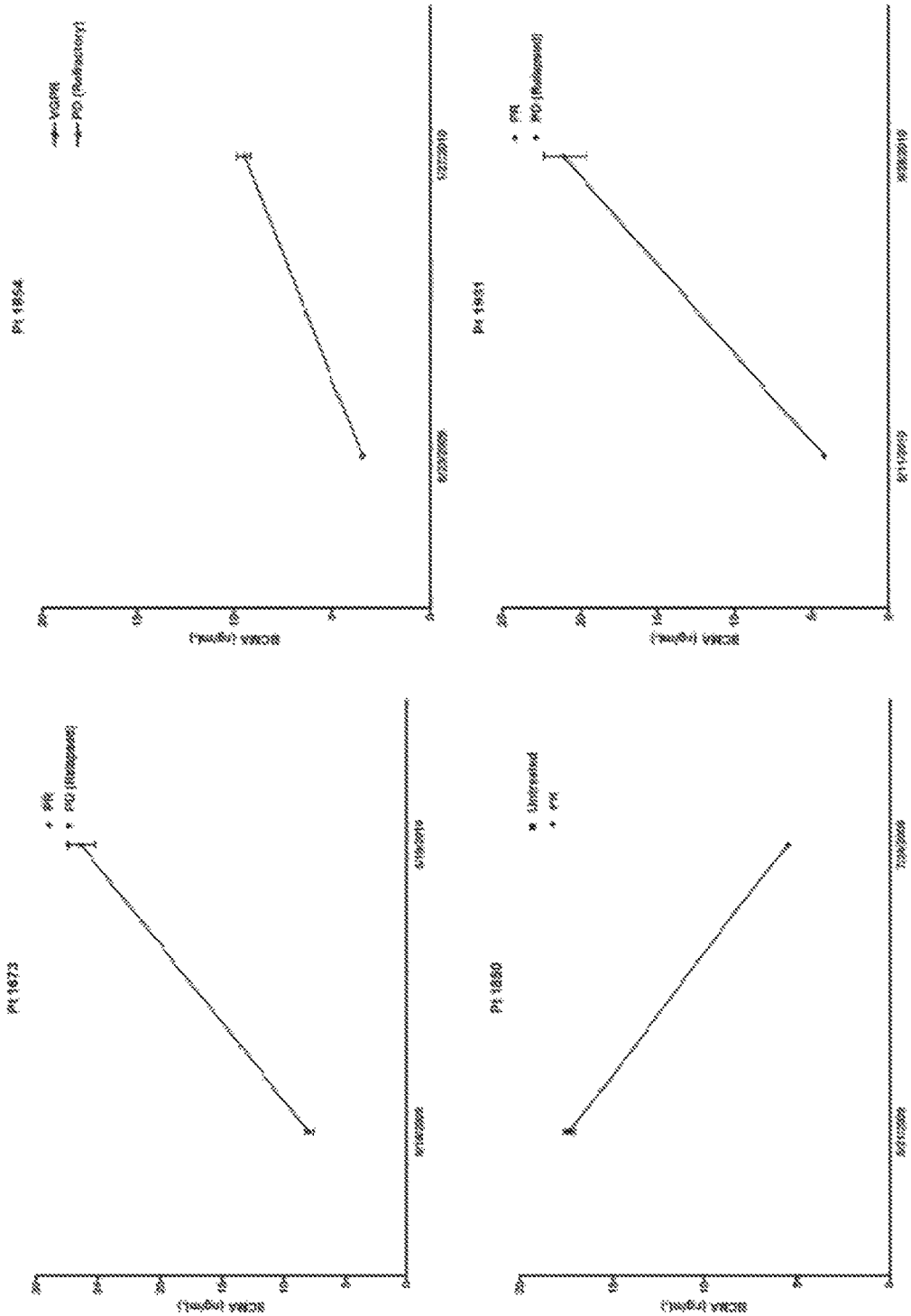
Figure 5C:
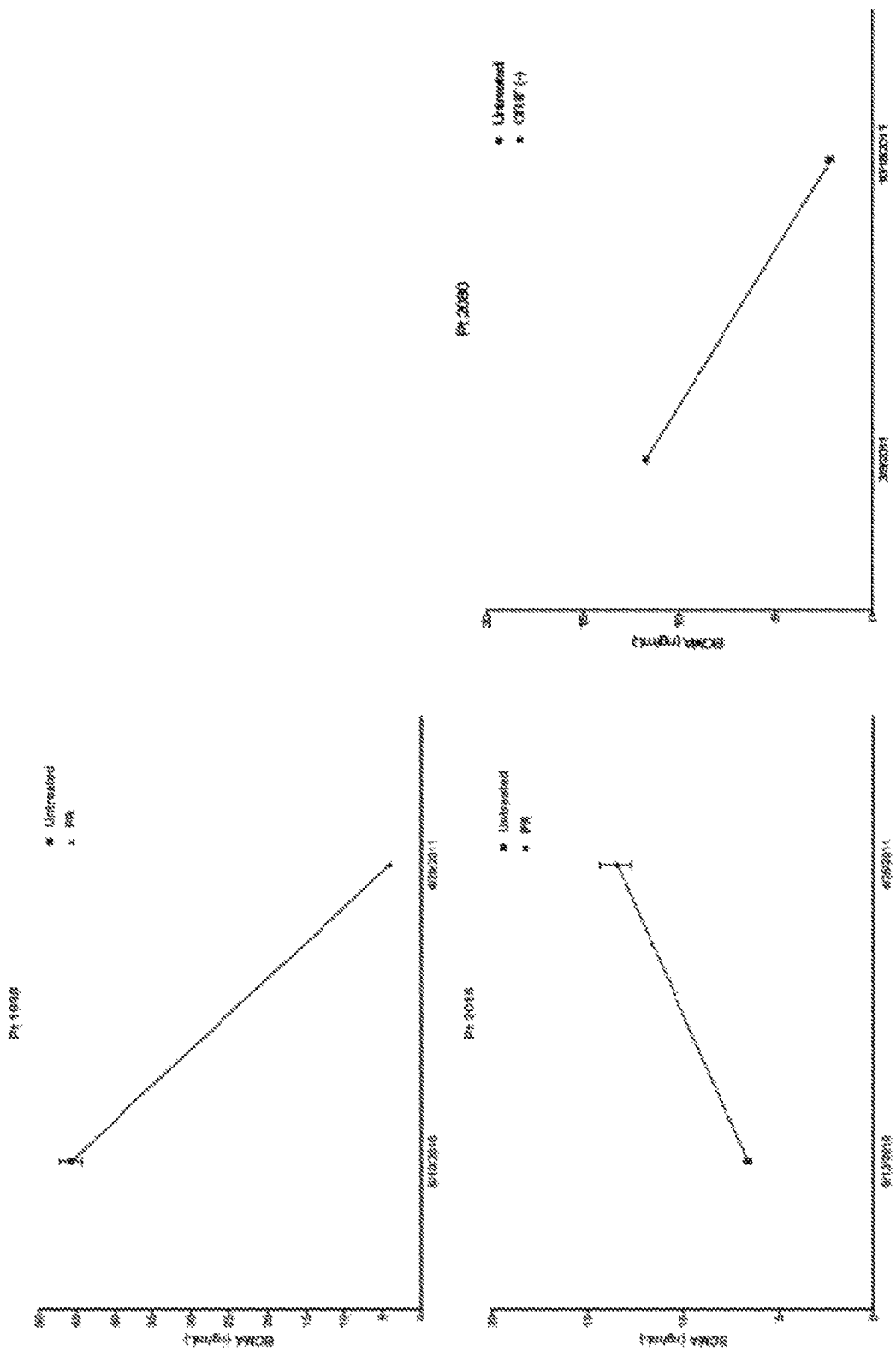
Figure 5E:
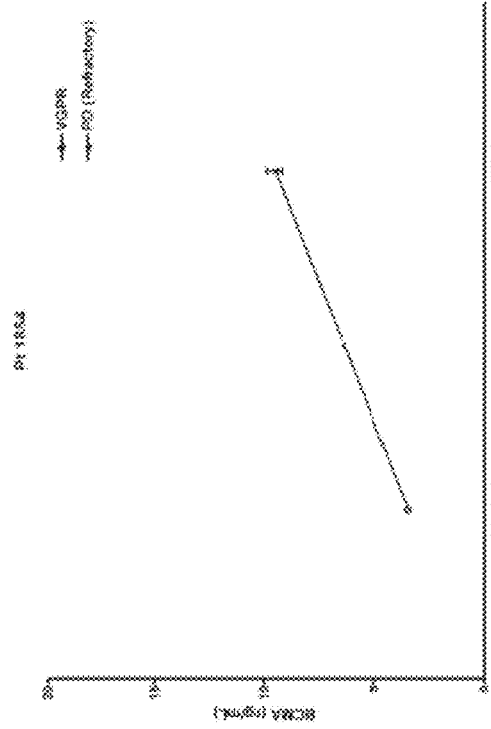
Figure 5G:
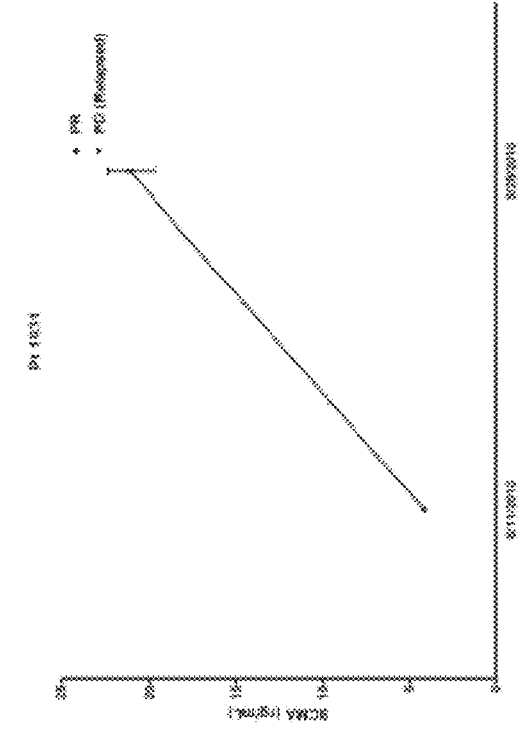
Figure 5D:
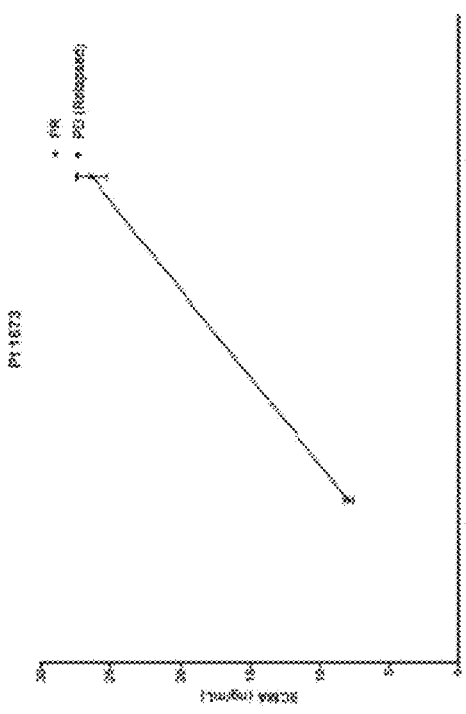
Figure 5F:
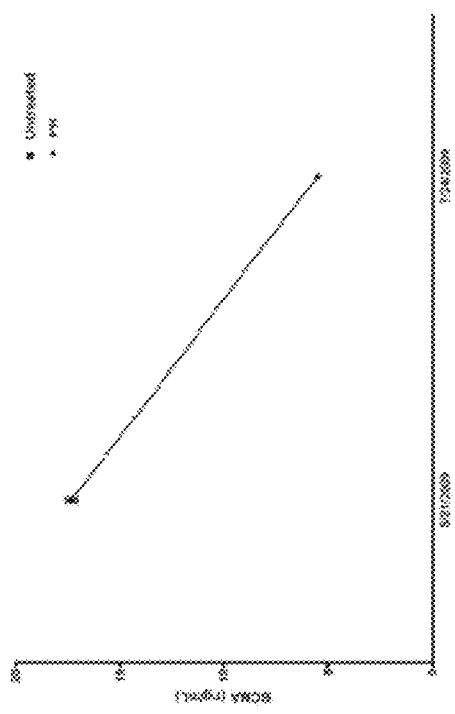
Figure 5H:
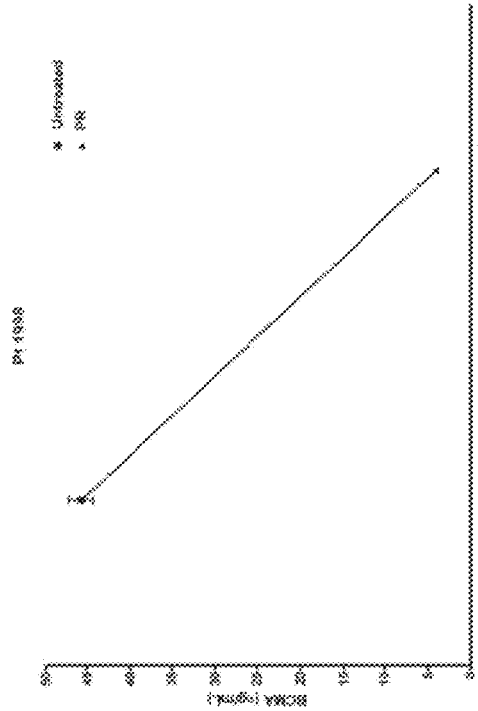
Figure 5I:
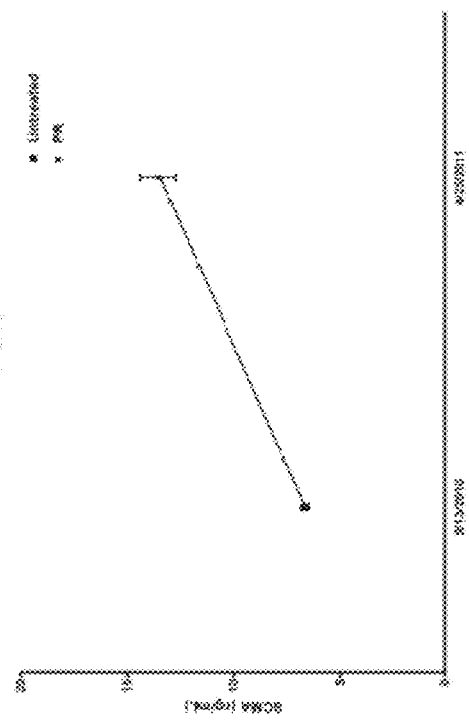
Figure 5J:
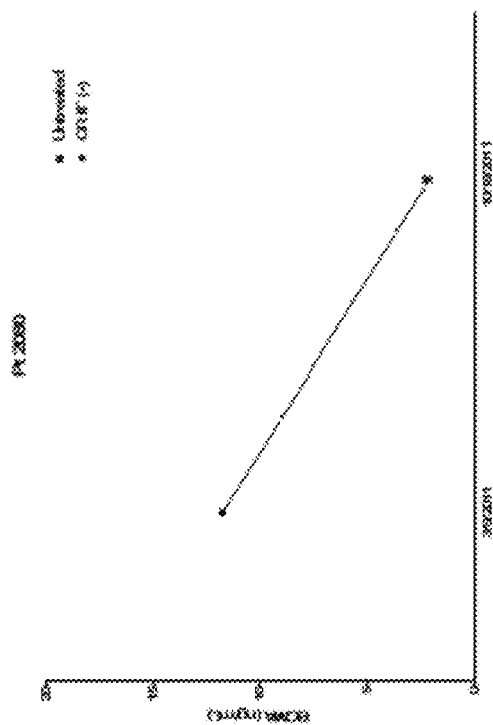

BCMA levels from serum and supernatants, of cultured BMMCs, of MM patients (n=14 samples) showed a strong correlation (r=0.82; FIG. 4). Changes in serum BCMA levels were found to correlate with changes in an individual patient's clinical status in response to anti-MM treatment.

Responsive (≥PR) patients (n=80 samples) had lower serum BCMA levels (median 4.06 ng/mL) than individuals (n=79 samples) showing progressive disease (median 19.76 ng/mL; P=0.0038; FIG. 3B). In addition, patients that achieved complete response (CR) (n=26) had lower BCMA levels (median, 2.09 ng/mL) than patients with very good partial response (VGPR) (n=16, median 3.33 ng/mL) or progressive response (PR) (n=38, median 5.44 ng/mL).

Patients responding to treatment showed decreases in BCMA levels whereas those with disease progression showed increases in BCMA levels (FIGS. 5A-5J). Regardless of the patient's clinical status, serum BCMA levels did not correlate with the use of specific anti-MM agents that were being administered (Table 1).

TABLE 1

BCMA levels and anti-MM treatments

|  | Steroids | Alkylators | Thalidomide | Lenalidomide | Bortezomib | PLD* |
|---|---|---|---|---|---|---|
| Responsive (R) | | | | | | |
| BCMA, median | 3.900587 | 4.48852 | 3.9902365 | 4.307007 | 3.532681 | 4.218058 |
| high | 229.5743 | 42.73638 | 229.5743 | 57.67272 | 57.67272 | 57.67272 |
| low | 0 | 0.858652 | 0.347363 | 0 | 0 | 0.870104 |
| # of samples | 61 | 10 | 12 | 15 | 52 | 16 |
| Progressive (P) | | | | | | |
| BCMA, median | 20.84389 | 12.98811 | 12.29372 | 20.50919 | 19.12083 | 38.81387 |
| high | 701.0412 | 42.72638 | 701.0412 | 301.1029 | 175.3668 | 76.41552 |
| low | 2.025315 | 0.858652 | 2.871958 | 2.237081 | 2.025315 | 7.88947 |
| # of samples | 44 | 11 | 10 | 16 | 31 | 6 |
| R and P | | | | | | |
| BCMA, median | 7.741305 | 7.599548 | 8.505564 | 8.749386 | 6.021121 | 6.955296 |
| high | 701.0412 | 42.73638 | 701.0412 | 301.1029 | 175.3668 | 76.41552 |
| low | 0 | 0.858652 | 0.347363 | 0 | 0 | 0.870104 |
| # of samples | 105 | 21 | 22 | 31 | 83 | 22 |

*PLD—PEGylated liposomal doxorubicin

Figure 6:
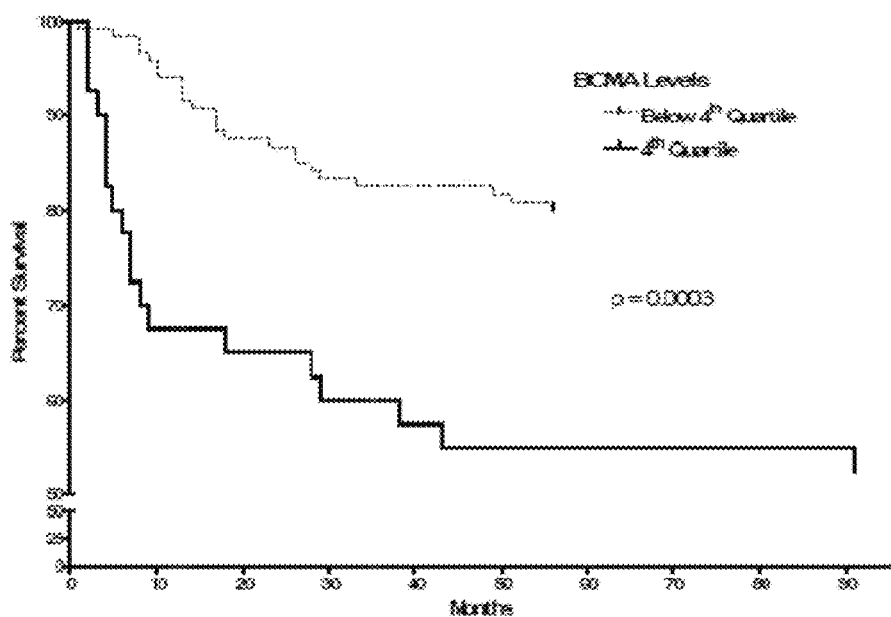
FIG. 6 shows that Kaplan-Meier survival of MM patients with serum BCMA levels in the highest quartile (25%) was shorter than the remaining patients. Among the MM patients (n=162), those with BCMA levels in the highest quartile (>24.56 ng/mL) showed a markedly shortened overall survival compared to the remainder of the patients.

With a median follow-up of 11 months (range, <1-83 months), MM patients (n=162) with BCMA levels above the median (10.85 ng/mL) showed a shortened survival compared to those with amounts below the median concentration (P=0.0014; FIG. 3C). In addition, patients in the highest quartile (≥24.56 ng/ml) showed a markedly shortened survival compared to the remainder of the patients (P=0.0003; FIG. 6).

Example 5

Polyclonal Anti-BCMA AB Blocked Detection of BCMA in Standards and Serum from MM Patients

Figure 7D:
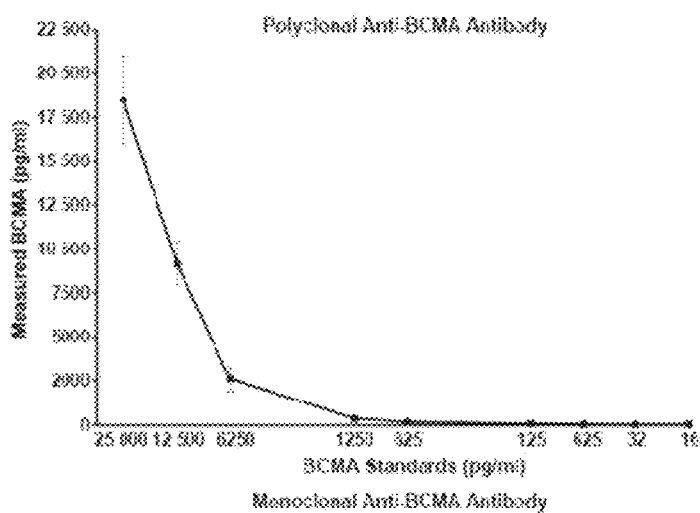

Sera from MM patients was incubated overnight at 4° C. with a polyclonal anti-BCMA Ab (catalogue #AF193; R&D Systems) and an ELISA was performed. The anti-BCMA Ab (400 ng/mL) blocked the detection of BCMA in the standards whereas an isotype-matched polyclonal goat control Ab at the same high concentration did not have any impact on detection of BCMA (FIG. 7A). When a 10-fold lower concentration of the blocking polyclonal anti-BCMA Ab (40 ng/mL) was used, BCMA became detectable, but only when high concentrations of the standards were present (FIG. 7B).

Similarly, BCMA was not detected in diluted and undiluted MM serum in the presence of a high concentration (100 ng/mL) of the blocking anti-BCMA Ab (FIG. 7C). BCMA levels were high in undiluted MM serum and decreased as the sample alone was diluted (FIG. 7C). When a 10-fold lower concentration of the blocking polyclonal anti-BCMA Ab (10 ng/mL) was used, BCMA became detectable, but at lower levels than in serum lacking the blocking Ab (data not shown). Thus, the exogenously added anti-BCMA Ab blocked the detection of BCMA identified with the standard anti-BCMA Ab used in the ELISA, indicated the specificity of this assay for detecting BCMA.

Example 6

Monoclonal Anti-BCMA AB Detected Similar Serum BCMA Levels as Detected with the Polyclonal Ab-Based ELISA

Figure 7E:
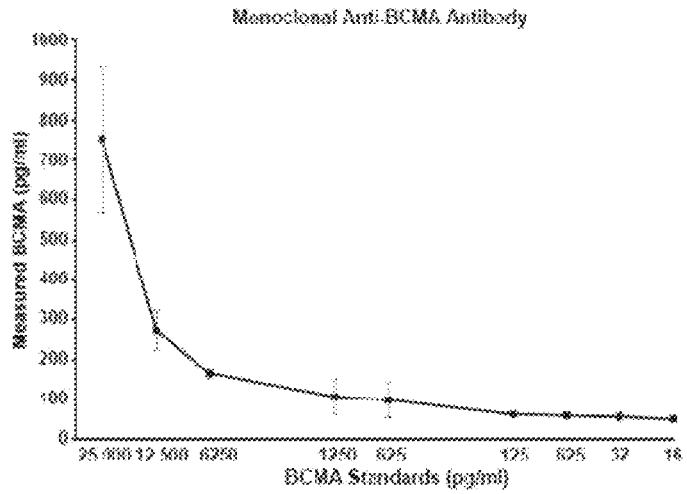
Figure 7F:
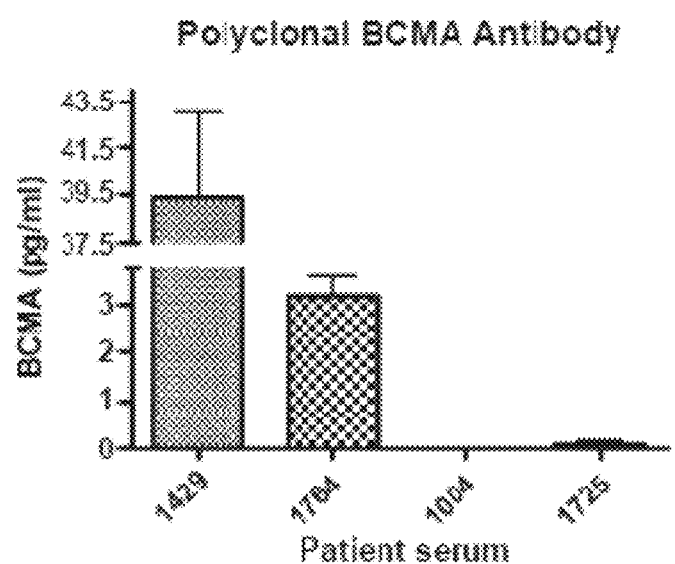
Figure 7G:
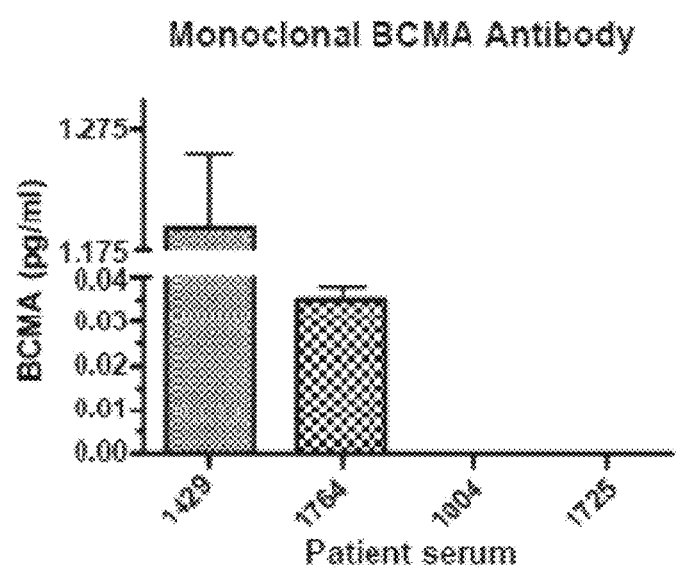

Plates were coated with a monoclonal anti-BCMA Ab (Sigma-Aldrich) as a capture Ab. BCMA standard antigens from the R&D Systems kit or patient serum was incubated with monoclonal Ab (mAb)-coated plates and then the standard protocol described in the R&D Systems kit was used. BCMA was detectable with the mAb (FIG. 7D) and the pattern of levels matched results obtained with the polyclonal Ab, when assessing the BCMA standards (FIG. 7E) and serum samples from MM and MGUS patients (FIGS. 7F-7G).

Example 7

SCID Mice Containing Human MM Xenografts Contained Human BCMA in their Serum and BCMA Levels Correlated with Tumor Volumes and Response to Anti-MM Therapy

Figure 8:
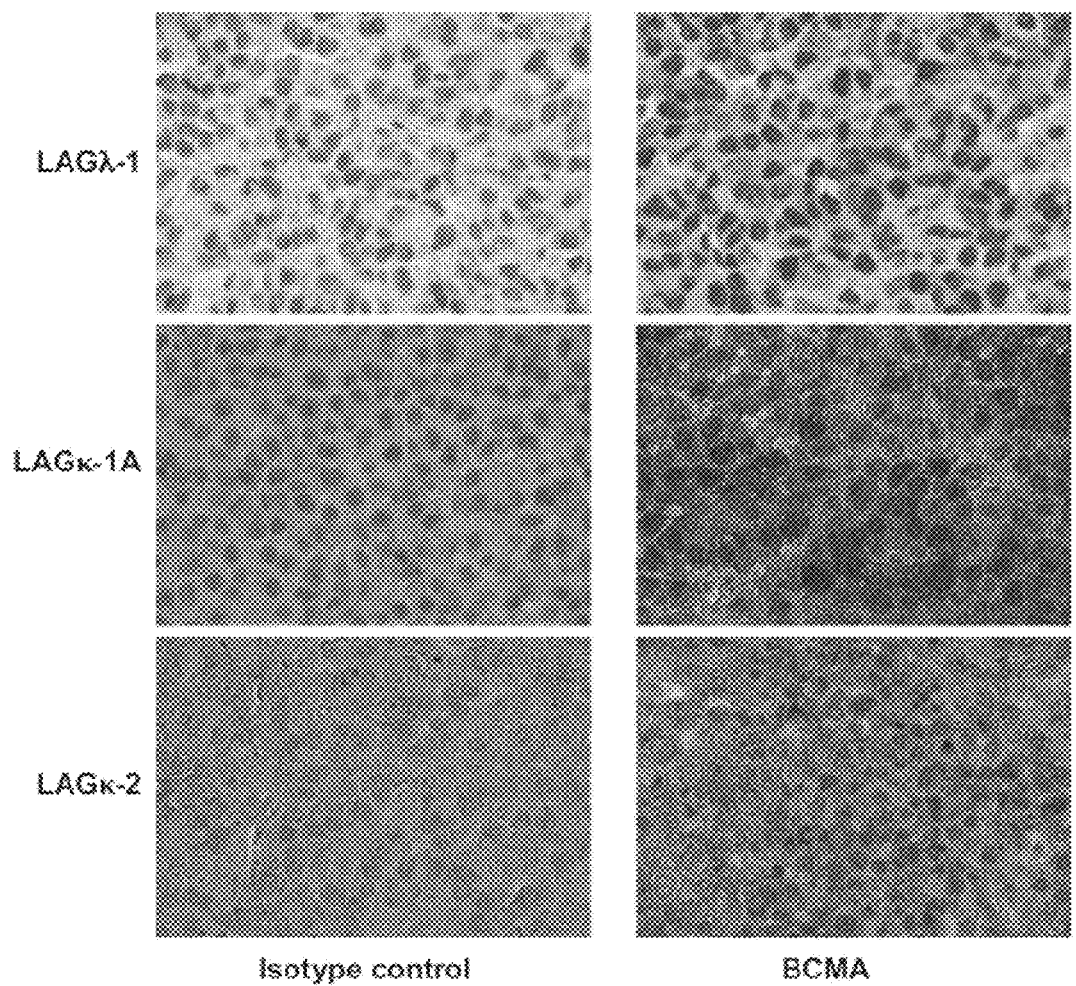
FIG. 8 shows positive immunohistochemical staining with anti-BMCA antibodies in human MM xenografts removed from CB17 SCID mice. Slides (original magnification ×100) were analysed using the Microsuite Biological Suite Program (Olympus BX51).

Human MM xenografts growing in SCID mice were used to determine whether BCMA that was detected in human MM serum and supernatants from cultured MM BMMCs was, in fact, derived from malignant cells. The only human cell type growing in the SCID mice with human MM were the tumor cells. MM tumors (LAGκ-2, LAGλ-1 and LAGκ-1A) were analyzed for human BCMA expression using immunohistochemistry (IHC). BCMA protein was detected in the three xenografts with anti-BCMA Ab, which does not bind to mouse BCMA (FIG. 8). No staining of other murine tissue was observed (data not shown).

Serum BCMA was not detected as the result of dead cells, either from natural tumor cell turnover or anti-MM treatment. Mice were allowed to grow non-paraprotein producing LAGκ-2 tumors to approximately 1000 mm$^3$ at which time the mice were treated with bortezomib and cyclophosphamide. Mice were bled 8-12 h following this combination treatment (n=7) or untreated controls (n=4). A decrease in both tumor volume (FIG. 9A; P=0.0006) and serum human BCMA levels (FIG. 9B; P<0.0001) were observed among drug-treated mice compared to untreated animals. A rise in serum BCMA levels from a possible release of membrane bound protein from dead cells was not observed following drug treatment. Thus, BCMA in the sera of the mice was from live plasma cells, and not the result of its release from dying MM cells.

Serum human BCMA levels also correlated with tumor growth, IgG levels and response to treatment in mice bearing another human MM xenograft, LAGλ-1. Untreated mice (n=4) had large tumor volumes and high serum IgG and BCMA levels. Mice receiving melphalan (3 mg/kg, n=4) twice weekly via i.p. injection showed smaller tumor volumes, IgG, and BCMA levels compared to untreated mice (tumor volumes: P<0.0001; hIgG, P=0.0033; BCMA, P=0.0055; FIGS. 10A-10C). Human BCMA was not detected in the serum of non-tumor bearing SCID mice (data not shown).

Example 8

Materials and Methods

Serum Collection and PB and BMMC Cultures

PB and BM aspirates were obtained from patients with MM, MGUS and age and gender-matched healthy control subjects. The study was approved by the Institutional Review Board (Western IRB BIO 001) and informed consent was obtained in accordance with the Declaration of Helsinki.

Patients were defined as having MGUS, MM patients as indolent MM or symptomatic disease, and treated patients as showing progressive or responsive disease (partial response (PR), very good (VG) PR, or complete response (CR)) according to the International Myeloma Working Group (IMWG) criteria (The International Myeloma Working Group, 2003; Rajkumar et al., 2011). Kaplan-Meier survival of MM patients was determined from the time of initial serum BCMA measurement to death or the date of last follow-up. Individual patients with multiple BCMA samples were analysed from the time of their first assessment.

Serum from a Corvac™ serum separator tube (Becton Dickinson, Franklin Lakes, N.J., USA) was isolated by centrifugation and stored at -80° C. PB and BM aspirates were collected in heparinized tubes and MCs were isolated using density-gradient centrifugation with Histopaque-1077 (Sigma-Aldrich, St. Louis, MO, USA). Cells were cultured in RPMI 1640 medium (Omega Scientific, Tarzana, CA, USA) supplemented with 10% fetal bovine serum, non-essential amino acids, 2 mmol/L glutamine, 1 mmol/L sodium pyruvate, 25 mmol/L HEPES, 200 units/mL penicillin, and streptomycin at 37° C. and 5% CO2.

Enzyme-Linked Immunosorbent Assay for Determination of BCMA Concentrations in Serum and Supernatant Fluid from BMMC Cultures Serum and supernatant samples were analyzed by BCMA enzyme-linked immunosorbent assay (ELISA) obtained from R&D Systems, Minneapolis, MN, USA (catalogue #DY193E). Serum samples were diluted 1:50 and the BCMA ELISA assay carried out according to the manufacturer's protocol. The ELISA plates were analysed using a Quant (Biotek Industries, Winooski, VT, USA) plate reader set to 450 nm with KC Junior software. Values represent the mean of triplicate samples on each specimen. This BCMA ELISA kit does not cross react with recombinant human APRIL or BAFF, recombinant human TACI/Fc or recombinant mouse BCMA/Fc or mouse BCMA.

Polyclonal Anti-BCMA Antibody (Ab) Blocking Experiment

B-cell maturation antigen standards were incubated with another polyclonal goat anti-human BCMA Ab (catalogue #AF193; R&D Systems) or control Ab at a high (400 ng/ml) or low (40 ng/ml) concentration overnight at 4° C. Polyclonal goat IgG Ab was used as an isotype control (catalogue #AB-108-C; R&D Systems). We also tested the ability of this polyclonal anti-BCMA Ab to block detection of BCMA from the serum of MM Patient 1056 following an overnight incubation and BCMA levels were assessed using the BCMA ELISA protocol described above.

Detection of BCMA with a Monoclonal Anti-BCMA Ab

B-cell maturation antigen standards or serum (diluted 1:50) from MM patients were incubated using a murine monoclonal anti-human BCMA Ab (catalogue #WH0000608M1; Sigma-Aldrich), instead of the polyclonal "capture Ab" used in the BCMA ELISA. The samples were then assayed according to the BCMA ELISA protocol.

MM Xenograft Studies

Six-week old CB17 SCID mice were obtained from Charles River Laboratories (Wilmington, MA, USA). Animal studies were conducted according to protocols approved by the Institutional Animal Care and Use Committee. To establish the CD38 and CD138-expressing LAGκ-2 tumor, a BM biopsy from a MM patient showing IgGκ paraprotein was implanted into the hind limb of a SCID mouse (Campbell & Berenson, 2008). Sera from mice containing the xenograft did not show human IgG or free κ light chains; and, thus, this xenograft was characterized as non-secretory. However, κ chains were observed in the cytosol of tumor cells using immunhistochemical (IHC) staining. The LAGκ-1A tumor was developed from a patient with an IgGκ-producing MM resistant to lenalidomide (Campbell & Berenson, 2008). The LAGλ-1 tumor was developed from a MM patient who showed IgGλ paraprotein (Campbell & Berenson, 2008). The xenografts were excised, sectioned into 20-40 mm$^3$ pieces, and implanted into the muscle. Seven days post-tumor implantation, mice were randomized into treatment groups. Animals were euthanized when the tumors reached 2.5 cm in diameter.

The proteasome inhibitor (PI) bortezomib (Millennium Pharmaceuticals, Cambridge, MA, USA) was used as a 1 mg/ml stock solution and diluted using 0.9% sodium chloride (NaCl). Bortezomib was administered i.v. at 0.75 mg/kg twice weekly. Cyclophosphamide (Florida Infusion, Palm Harbor, FL, USA) was dissolved from a stock solution of 20 mg/mL with NaCl and administered at 10 mg/kg via oral gavage once weekly. Melphalan (Sigma-Aldrich) at 3 mg was dissolved in 100 µL Acid-EtOH (47 µl concentrated HCl and 1 ml 100% EtOH) and diluted to 1 mL with phosphate-buffered saline (PBS) to generate a 3 mg/mL stock solution. The drug was administered via intraperitoneal (i.p.) injection twice weekly at a dose of 3 mg/kg.

Tumors were measured using standard calipers and the formula for an ellipsoid volume was applied ($4/3\pi \times$[width/$2]^2 \times$[length/2]). Tumor growth and IgG curves were analyzed in terms of treatment group means and standard error.

Mice were bled weekly via retro-orbital sinus to determine human IgG and BCMA levels. Samples were spun at 10,000 rpm for 5 min and serum was collected. The human IgG ELISA kit (Bethyl Laboratories, Montgomery, TX, USA) was used according to the manufacturer's specifications. Absorbance at 450 nm with a reference wavelength of 550 nm was determined on a µQuant microplate spectrophotometer with KC Junior software (Bio-Tek Instruments, Winooski, VT, USA). The human BCMA ELISA kit (R&D Systems) was used to determine serum protein levels.

Immunohistochemical Analysis

B-cell maturation antigen protein expression was determined in MM and normal BMMCs and in our human MM xenografts. For the xenografts, 5 m sections were cut after fixation in 4% paraformaldehyde. For the BMMCs, the cells were fixed with 1% paraformaldehyde and $1\times10^5$ cells/slide were cytopsun. The slides were blocked with 0.05% Tween-20 PBS (PBST) and 3% bovine serum albumin (BSA) for 1 h at room temperature (RT). The samples were exposed to the anti-human BCMA Ab (5 µg/mL) at 4° C. overnight. The slides were washed three times with TBST and treated with horseradish peroxidase conjugated with either anti-mouse, anti-rabbit or anti-goat antibodies (KPL, Gaithersburg, MD, USA) diluted 1:500 in TBST at RT for 2 h. The slides were washed three times in TBST and placed in 3-amino-9-ethylcarbazole (AEC) buffer for 5 min, and color was detected using an AEC kit (Vector Laboratories, Burlingame, CA, USA). For light chain staining, BMMCs were resuspended in 100 µL PBS and cytopsun on slides. The samples were blocked with 3% BSA before the Ab was added to prevent non-specific binding. Goat anti-human λ light chain Ab (Sigma-Aldrich), anti-human κ light chain Ab (Sigma-Aldrich) or isotype control Ab (R&D System) was added to the corresponding samples. These antibodies were incubated overnight at 4° C. On the following day, the antibodies were washed with 0.05 mol/L TBST buffer. The samples were then treated with 10% $H_2O_2$ methanol before the secondary Ab. The samples were then incubated with peroxidase-labeled rabbit anti-goat Ab (KPL) for 2 h at RT and then washed. Peroxidase substrate (Vector Laboratories) was added to the samples for 30 min. The cells were stained with haematoxylin for 1 min, and the samples were mounted. BCMA and λ and κ light chain expression was determined using a light microscope (Olympus BX51; Olympus, San Diego, CA, USA). Haematoxylin and eosin (H&E) staining was performed on BMMCs using standard staining procedures.

Statistical Analyses

Statistical significance of differences observed in supernatant, serum and xenograft studies was determined using a Student's t-test. The minimal level of significance was $P<0.05$. Statistical analysis was determined using GRAPHPAD PRISM version 4.03 for Windows (GraphPad Software, San Diego, CA, USA).

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of assaying for BCMA, comprising:
   (a) providing a first biological sample obtained from a patient diagnosed with chronic lymphocytic leukemia (CLL) and a second biological sample from the patient diagnosed with CLL,
   (b) detecting a first amount of BCMA polypeptide or fragment thereof in the first biological sample, and
   (c) detecting a second amount of BCMA polypeptide or fragment thereof in the second biological sample;
   wherein the first biological sample and the second biological sample are each independently:
      (i) a serum sample obtained from the patient's blood,
      (ii) a plasma sample obtained from the patient's blood,
      (iii) a supernatant sample obtained from culture of the patient's bone marrow mononuclear cells, or
      (iv) a supernatant sample obtained from culture of the patient's peripheral blood mononuclear cells.

2. The method of assaying for BCMA according to claim 1, wherein the first biological sample is a first serum sample obtained from the subject's blood, the first serum sample being obtained prior to administration of a treatment for CLL, and wherein the second biological sample is a second serum sample obtained from the subject's blood, the second serum sample being obtained after administration of a treatment for CLL.

3. The method of assaying for BCMA according to claim 1, wherein the first biological sample is a first plasma sample obtained from the subject's blood, the first plasma sample being obtained prior to administration of a treatment for CLL, and wherein the second biological sample is a second plasma sample obtained from the subject's blood, the second plasma sample being obtained after administration of a treatment for CLL.

4. The method of assaying for BCMA according to claim 1, wherein the first biological sample is a first supernatant sample obtained from culture of the patient's bone marrow mononuclear cells, the first biological sample being obtained prior to administration of a treatment for CLL to the patient, and
   wherein the second biological sample is a second supernatant sample obtained from culture of the patient's bone marrow mononuclear cells, the second biological sample being obtained after to administration of a treatment for CLL to the patient.

5. The method of assaying for BCMA according to claim 1, wherein the first biological sample is a first supernatant sample obtained from culture of the patient's peripheral blood mononuclear cells, the first biological sample being obtained prior to administration of a treatment for CLL to the patient, and
   wherein the second biological sample is a second supernatant sample obtained from culture of the patient's peripheral blood mononuclear cells, the second biological sample being obtained after to administration of a treatment for CLL to the patient.

6. The method of assaying for BCMA according to claim 1, wherein the detecting steps are performed using enzyme-linked immunosorbent assay (ELISA).

7. The method of assaying for BCMA according to claim 1, wherein the detecting steps are performed using radioimmunoassay (RIA).

8. The method of assaying for BCMA according to claim 1, wherein the detecting steps are performed using enzyme immunoassay (EIA).

9. The method of assaying for BCMA according to claim 1, wherein the detecting steps are performed using fluorescence immunoassay (FIA).

10. The method of assaying for BCMA according to claim 1, wherein the detecting steps are performed using luminescence immunoassay (LIA).

11. The method of assaying for BCMA according to claim 1, wherein the detecting steps are performed using lateral flow assay.

12. The method of assaying for BCMA according to claim 1, wherein the detecting steps are performed using strip assay.

13. The method of assaying for BCMA according to claim 2, wherein the second amount being greater than the first amount indicates that said CLL is progressing, and wherein the first amount being greater than the second amount indicates that said CLL is entering remission or responding to treatment.

14. The method of assaying for BCMA according to claim 3, wherein the second amount being greater than the first amount indicates that said CLL is progressing, and wherein the first amount being greater than the second amount indicates that said CLL is entering remission or responding to treatment.

15. The method of assaying for BCMA according to claim 4, wherein the second amount being greater than the first amount indicates that said CLL is progressing, and wherein the first amount being greater than the second amount indicates that said CLL is entering remission or responding to treatment.

16. The method of assaying for BCMA according to claim 5, wherein the second amount being greater than the first amount indicates that said CLL is progressing, and wherein the first amount being greater than the second amount indicates that said CLL is entering remission or responding to treatment.

17. A method of determining progression of chronic lymphocytic leukemia (CLL), comprising:
   (a) providing a first biological sample obtained from a patient diagnosed with CLL and a second biological sample from the patient diagnosed with CLL,
   (b) detecting a first amount of BCMA polypeptide or fragment thereof in the first biological sample, and
   (c) detecting a second amount of BCMA polypeptide or fragment thereof in the second biological sample;
   wherein the first biological sample and the second biological sample are each independently:
      (i) a serum sample obtained from the patient's blood, or
      (ii) a plasma sample obtained from the patient's blood;
   further wherein the first biological sample is obtained prior to administration of a treatment for CLL and the second biological sample is obtained after administration of the treatment for CLL; and
   wherein the second amount being greater than the first amount indicates that said CLL is progressing, and wherein the first amount being greater than the second amount indicates that said CLL is entering remission or responding to treatment.

* * * * *